(12) United States Patent
Cardell et al.

(10) Patent No.: US 12,324,766 B2
(45) Date of Patent: Jun. 10, 2025

(54) LID FOR MEDICAL IMPLANT

(71) Applicant: OstomyCure AS, Oslo (NO)

(72) Inventors: Mats Erik Kindahl Cardell, Sollentuna (SE); Erik Elwing, Jönköping (SE); Jimmy Carl Henrik Gidö Schön, Ballstad (NO)

(73) Assignee: OstomyCure AS, Oslo (NO)

( * ) Notice: Subject to any disclaimer, the term of this patent is extended or adjusted under 35 U.S.C. 154(b) by 0 days.

(21) Appl. No.: 18/503,716

(22) Filed: Nov. 7, 2023

(65) Prior Publication Data
US 2024/0065880 A1 Feb. 29, 2024

Related U.S. Application Data

(60) Continuation of application No. 17/742,051, filed on May 11, 2022, now Pat. No. 11,877,946, which is a division of application No. 16/095,687, filed as application No. PCT/EP2017/064695 on Jun. 15, 2017, now Pat. No. 11,357,658.

(51) Int. Cl.
*A61F 5/445* (2006.01)
*A61F 5/44* (2006.01)

(52) U.S. Cl.
CPC ............ *A61F 5/445* (2013.01); *A61F 5/4407* (2013.01); *A61F 2005/4455* (2013.01)

(58) Field of Classification Search
CPC . A61F 5/445; A61F 2005/4455; A61F 5/4407
See application file for complete search history.

(56) References Cited

U.S. PATENT DOCUMENTS

| | | | |
|---|---|---|---|
| 4,410,102 A | 10/1983 | Lutzker |
| 5,041,102 A | 8/1991 | Steer et al. |
| 5,269,433 A | 12/1993 | Piquerez |
| D419,370 S | 1/2000 | Busick et al. |
| D547,651 S | 7/2007 | Simpson, Jr. et al. |
| D567,021 S | 4/2008 | Bach et al. |
| D587,999 S | 3/2009 | Schulthess |
| D588,870 S | 3/2009 | Rasmussen |
| D614,897 S | 5/2010 | Morand |
| D630,044 S | 1/2011 | Lane et al. |
| 8,663,334 B2 | 3/2014 | Viscardi et al. |

(Continued)

FOREIGN PATENT DOCUMENTS

| | | |
|---|---|---|
| CN | 102596115 A | 7/2012 |
| CN | 205285836 U | 6/2016 |

(Continued)

OTHER PUBLICATIONS

India Office Action examination report dated Nov. 18, 2022, Application No. 202118054773 dated Nov. 18, 2022.

(Continued)

*Primary Examiner* — Andrew J Mensh
*Assistant Examiner* — Meagan Ngo
(74) *Attorney, Agent, or Firm* — DINSMORE & SHOHL LLP

(57) ABSTRACT

A lid for a medical implant has a first part, a second part and engaging means. The second part is rotatable relative to the first part such that, in use, rotation of the second part relative to the first part causes the engaging means to engage with and attach the lid to the implant.

18 Claims, 17 Drawing Sheets

(56) References Cited

U.S. PATENT DOCUMENTS

| | | | |
|---|---|---|---|
| D721,436 S | 1/2015 | Ting et al. | |
| D730,183 S | 5/2015 | Fahl | |
| D731,064 S | 6/2015 | Seto et al. | |
| D743,552 S | 11/2015 | Bronnimann et al. | |
| D746,683 S | 1/2016 | Fahl | |
| D780,921 S | 3/2017 | Burkinshaw et al. | |
| D784,536 S | 4/2017 | Freudenthal | |
| D788,925 S | 6/2017 | Brönnimann et al. | |
| D796,029 S | 8/2017 | Hanuka et al. | |
| 9,750,543 B2 | 9/2017 | Biedermann et al. | |
| D799,037 S | 10/2017 | Kubiak et al. | |
| D802,326 S | 11/2017 | Beaver | |
| D802,407 S | 11/2017 | Foerster, Jr. | |
| 9,820,859 B2 | 11/2017 | Gervasi et al. | |
| D804,668 S | 12/2017 | Burkinshaw et al. | |
| 2007/0244452 A1 | 10/2007 | Axelsson et al. | |
| 2012/0123361 A1* | 5/2012 | Johansson | A61F 5/445 604/338 |
| 2012/0179124 A1 | 7/2012 | Nguyen-Demary et al. | |
| 2012/0245535 A1* | 9/2012 | Jacobsson | A61F 5/445 604/264 |
| 2015/0141944 A1* | 5/2015 | Hanuka | A61F 5/442 604/338 |
| 2015/0209173 A1 | 7/2015 | Kratky | |
| 2018/0235800 A1* | 8/2018 | Lee | A61F 5/445 |

FOREIGN PATENT DOCUMENTS

| | | |
|---|---|---|
| EP | 0 947 367 A1 | 10/1999 |
| EP | 2 424 473 B1 | 5/2017 |
| ES | 2320205 T3 | 5/2009 |
| GB | 05362 A | 10/1911 |
| GB | 884107 A | 12/1961 |
| GB | 2 129 783 A | 5/1984 |
| GB | 2 482 048 A | 1/2012 |
| WO | 97/44259 A1 | 11/1997 |
| WO | 2006/046210 A1 | 5/2006 |
| WO | 2009/029610 A1 | 3/2009 |
| WO | 2011/039517 A1 | 4/2011 |
| WO | 2014/140344 A1 | 9/2014 |
| WO | 2015/137663 A1 | 9/2015 |

OTHER PUBLICATIONS

Search Report and Written Opinion, International Application No. PCT/EP2017/064695, dated Jan. 25, 2018.

Search Report, Application No. GB 1610527.2, dated Dec. 12, 2016.

Search Report, Application No. GB 1610527.2, claims 17-19, dated Apr. 18, 2017.

Search Report, Application No. GB 1610527.2, claims 20-22, dated Apr. 18, 2017.

* cited by examiner

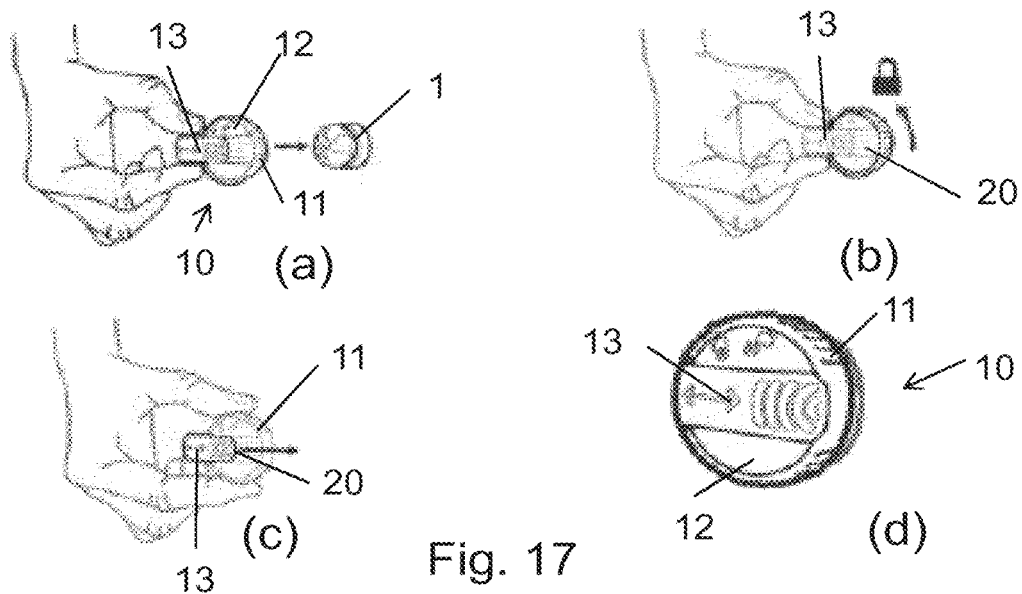
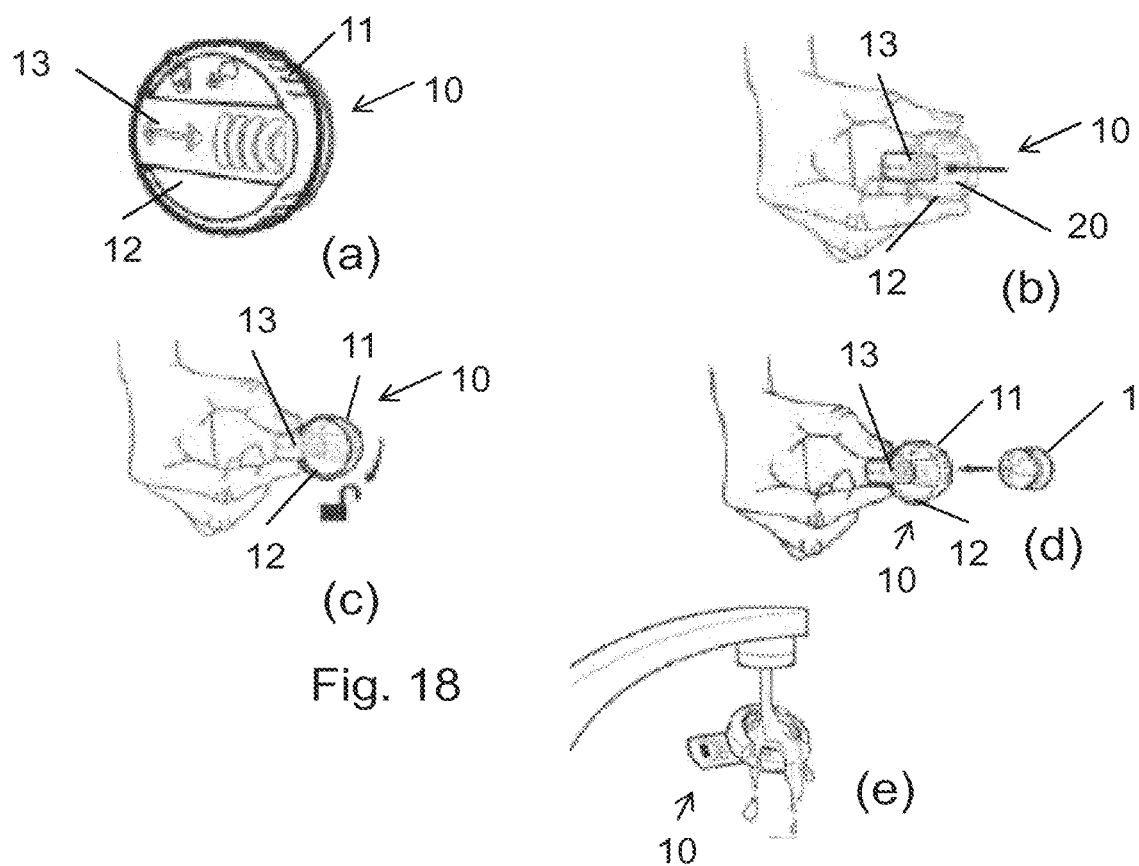
Fig. 17
Fig. 18

LID FOR MEDICAL IMPLANT

CROSS-REFERENCE TO RELATED APPLICATIONS

This application is a continuation of Ser. No. 17/742,051 filed May 11, 2022, which is a divisional of U.S. application Ser. No. 16/095,687 filed Oct. 22, 2018, which is a 371 filing of International Application No. PCT/EP2017/064695 filed Jun. 15, 2017, which claims priority to British Application No. 1610527.2 filed Jun. 16, 2016, the disclosures of each of which are hereby incorporated by reference in their entirety.

FIELD OF THE INVENTION

The present invention relates to a lid or closure device. In particular, it relates to a lid or closure device for a medical implant, more particularly for an ostomy implant.

BACKGROUND OF THE INVENTION

Ileostomy and colostomy are common operations which may be necessitated, for example, by malignancy or chronic bowel inflammation. The surgery is called an ileostomy if the colon and rectum are removed and a colostomy if the rectum alone is removed. Similarly an abdominal urostomy is created when the urinary bladder has to be removed due to, for example, bladder cancer. In these operations, a stoma is formed in the abdominal wall to which a bowel segment is connected.

Ostomy is a generic term for any such procedure where a stoma is created.

The stoma, in most cases, has to be connected to a bag for the collection of bodily waste. However, instead of a conventional ileostomy, it is possible to make a reservoir known as a "Kock pouch" from the distal part of the ileum. The pouch is formed in such a way that a nipple valve is created which serves to close the reservoir, whilst allowing it to be drained intermittently by means of a catheter. This is an example of a so-called continent ileostomy (CI) and it was formerly an attractive alternative to conventional ileostomy but is now rarely used. The complexity of the procedure and the high potential for complications—most of them related to dysfunction of the continence nipple valve—has deterred many surgeons from adopting the operation today.

The ileopouch anal anastomosis (IPAA) is today the gold standard worldwide for these patients but, as with a CI, this operation is also risky and failures are common, mostly leading to pouch excision with loss of bowel. Conversion of a failed IPAA to a CI would be a preferable option but, again, surgeons are reluctant to perform this complex and unreliable technique. Likewise, conversion of a malfunctional orthotopic neobladder or Bricker urostomy would be desirable.

It is known to provide an implant to facilitate connection of a stoma to a lid or bag, for example.

For example, and as illustrated in FIGS. 1 and 2, the applicant's earlier application WO 2014/140344 A1 discloses a percutaneous ostomy implant 1 comprising a tubular interior section 2, formed mainly of mesh, and a circular, radially-extending anchoring flange or dermal anchor 3.

The implant 1 is designed to be implanted through the abdominal wall of a patient and to receive a bowel section drawn through it. Serosal tissue from the bowel section can then grow into the implant 1, through the mesh, and attach or grow into surrounding dermal tissue. This can provide a secure, stable, leak-proof and well-vascularised tissue-implant junction.

The tubular interior section 2 is attached to an exterior section 4, which, when the implant 1 is implanted in a patient, protrudes from the patient's body. A groove 6 around the exterior circumference of the exterior section 4 allows a lid, bag or other device (not shown) to be attached to the implant 1.

Once an implant has been implanted into a patient, it is necessary to close it in some way, or to sealingly connect it to some form of evacuation means (e.g. a bag or catheter), to prevent leakage of waste from the stoma, and to allow waste to be collected and/or disposed of cleanly. This means that usually some form of lid needs to be attached to the external end of the implant.

The applicant's earlier application WO 2006/046210 A1 discloses a detachable lid for an implant with mounting means (e.g. a groove or ridge) arranged such that the detachable lid can be mounted onto and removed from an external end of the implant by sliding the lid in a direction perpendicular to the longitudinal axis of the implant.

However, a problem with this method of mounting a lid on an implant is that it may cause forces to be exerted on the implant which can damage the tissue-implant junction. It can also be difficult for a patient to mount a lid in this way.

A further problem is that with this sliding method of attachment, it may be difficult for the lid to seal properly, i.e. in a leak-tight way, with the implant.

WO 2006/046210 A1 also discloses a connecter for connecting an ostomy bag to the implant. The connector is arranged to slide the lid off of the implant and to connect the bag to the implant.

In the applicant's more recent application WO 2011/039517 A1, a medical closure device is disclosed comprising a coupling part and a closure part (e.g. a lid or cap). The coupling part can be attached to a medical device such as an implant and the closure part can then be attached to the coupling part to close the implant. The coupling part is a circumferential flexible member delimiting a coupling opening, and is configurable between a relaxed configuration where the coupling opening cannot pass over the medical device and a stressed configuration where the coupling opening of the coupling part can pass over the medical device. Thus, if the coupling part is squeezed, it will deform from its relaxed configuration into a stressed configuration in which it can be passed over the end of the implant. When pressure is released (i.e. the squeezing is stopped), the coupling part will attempt to return to the relaxed configuration, thus gripping the end of the implant. The reverse procedure can be performed to remove the coupling part.

However, a problem with this attachment mechanism is that it may be possible for the coupling part to become detached from the implant, unintentionally or accidentally, for example if, e.g. by leaning on an object, pressure is applied to the coupling part causing it to be squeezed into its stressed configuration whereby it may become detached from the implant.

The closure device of WO 2011/039517 A1 is also relatively wide and, when attached to an implant, extends down close to the patient's skin such that there is a risk of abrasion and irritation.

Attaching the closure part to the coupling part requires two hands, which may be problematic for a user. Also, as the closure device comprises two separate parts (the coupling part and the closure part) there is greater chance of one part becoming lost or dropped, compared with a closure device made of a single part. Handling may also be more inconvenient.

Furthermore, there is a possibility with this closure device that it could become attached to the implant (locked) in an incorrect position, such that it is not properly seated and sealed on the implant. For example, often a user cannot see the lid-implant interface (e.g. due to clothing or stomach being in the way) and so they may attach or lock the closure device onto the implant in an incorrect position.

SUMMARY OF THE INVENTION

According to a first aspect of the present invention, there is provided a lid for a medical implant, the lid comprising a first part, a second part and engaging means, wherein the second part is rotatable relative to the first part (or the first part is rotatable relative to the second part) such that, in use, rotation of the second part relative to the first part (or vice versa) causes the engaging means to engage with and attach the lid to the implant.

Thus, according to the invention, the second part of the lid can be rotated with respect to the first part (or vice versa) to cause the lid to be engaged with and attached to the implant. Accordingly, one part of the lid (e.g. the first part) may be kept stationary with respect to the implant while the lid is being attached thereto. This can reduce or eliminate any forces applied to the implant during attachment, thereby helping to reduce or eliminate potential damage to an implant-tissue junction. In addition, a lid with such an attachment mechanism provides a relatively straightforward and easy way for a user to attach the lid to an implant and accidental removal of the lid may be minimised or prevented.

Since the lid may be attached to, or detached from, an implant simply by the rotation of one of its parts, it may be possible to attach the lid single-handedly. This has the benefit of course that a second hand may be used to hold other items which may be needed, for example, after a lid has been removed (e.g. for evacuation/cleaning). (Alternatively, of course, two hands may be used).

Further, since the lid may be attached to, or detached from, an implant simply by the rotation of one of its parts, users with, e.g., arthritis, weak hands or small hands may be able to perform this procedure.

The medical implant with which the lid may be used could, for example, be an ostomy implant and the present invention is indeed particularly suited for this purpose. However, the lid is not limited to use with ostomy implants, or indeed with any other kind of medical implant, and could be used for any medical implant or indeed to cover any other structure in or over which it is useful to provide a lid with such an attachment mechanism, for example. Examples of medical implants with which this lid could be used may include, but are not limited to, colostomy implants, urostomy implants and gastrostomy implants, for example. A further example of a medical system with an implant, with which this lid could be used, is an enteral feeding system (e.g. delivery of nutrition directly into the stomach through a permanent transcutaneous catheter).

When attached to an implant, the lid, particularly the engaging means, is preferably strong enough and secure enough such that it can withstand overpressures inside the patient (e.g. due to a build-up of gas).

The simple mechanism described above means that the lid may be, and preferably is, relatively thin. For example, the lid may have a depth of 2.0 cm or less, 2.8 cm or less, 2.6 cm or less, 2.4 cm or less, 2.2 cm or less, 2.0 cm or less, 1.8 cm or less, 1.6 cm or less, 1.4 cm or less, 1.2 cm or less, 1.0 cm or less. Providing such a thin lid means that, in use, the lid is less likely to catch on other objects that a user may come into contact with such as tables, clothing, door frames, belts, etc.

The lid may have a smooth, rounded top or outer surface, curving down to a point at which it would contact a user's skin. In this way, the lid would have no corners or projecting parts which could catch against other objects.

The first part, the second part and the engaging means are preferably arranged such that, in use, rotation of the second part relative to the first part (or vice versa) causes the first part to press against the engaging means. This arrangement can provide a simple mechanism by which rotation of the second (or first) part causes engaging of the engaging means with an implant.

The engaging means could be or comprise any form of engagement mechanism or engager.

The engagement means is preferably located in the second part. The engaging means could be a part of the second part or, alternatively, the engaging means could be a separate component which, for example, is provided within the second part.

The engaging means could be or comprise any kind of engagement part e.g. that is suitable for engaging with an implant. For example, the engaging means could comprise one or more protruding engagement means or protrusions (e.g. a projection, ridge, bump, pin, hook) which may be arranged and/or dimensioned so as to fit in a corresponding receiving part (e.g. a groove, slot, hole or recess) provided on the implant.

Alternatively, or additionally, the engaging means could comprise one or more recesses or cavities (e.g. groove, slot, hole), provided, for example, inside the second part, which recesses or cavities may be arranged and/or dimensioned so as to receive or fit over a protruding engagement means or protrusion (e.g. a projection, ridge, bump, pin or hook) provided on the implant.

Preferably, the engaging means comprises one or more components which are separate from (not integrally formed with) the second part and is/are preferably contained within the second part but movable, e.g. at least to some extent, with respect to the second part.

Alternatively or additionally, the engaging means may comprise one or more fixed or integral engaging components (e.g. fixed to or integrally formed with the second part) such as a protrusion (e.g. a projection, ridge, bump, pin or hook) or receiving part (e.g. a groove, slot, hole or recess).

The engaging means is preferably arranged such that when the second part is rotated with respect to the first part (or vice versa), the engaging means is made to protrude into an engagement recess or cavity provided on the implant.

Alternatively, the engaging means could be arranged such that when the second part is rotated with respect to the first part (or vice versa), the engaging means is made to protrude over, around or through an engagement protrusion provided on the implant.

In a preferred embodiment, the engaging means comprises one or more, preferably three, pins. Where more than one pin is provided, the two or more pins may be arranged at, preferably equal, spacings around the second part such that the two or more pins can engage with an implant around its circumference.

Preferably the one or more pins are arranged such that it is a longitudinal side of the one or more pins that would engage with the implant. However, in an alternative embodiment, the one or more pins could be arranged such that it is an end of each of the one or more pins that would engage with the implant.

The pin or pins is/are preferably supported by the second part, and preferably movable, at least to some extent, with respect to second part.

The pin or pins is/are preferably straight, e.g. with a circular cross-section and preferably rounded ends.

Preferably, the first part, second part and engaging means are arranged such that as the second part is rotated with respect to the first part (or vice versa), the first part also moves further into or onto the second part.

Preferably, the first part, second part and engaging means are further arranged such that as the first part moves further into or onto the second part, the first part exerts a force on, pushes or presses the engaging means, such that the engaging means can engage with an implant.

Thus, by rotating the second (or first) part, the engaging means can be made to engage with an implant.

In addition, preferably, the first part, second part and engaging means are arranged such that as the first part moves further into or onto the second part, and the first part exerts a force on, pushes or presses the engaging means, the engaging means engages with the implant by being moved radially inwards towards the implant and/or (then) upwards, preferably both. By causing the engaging means to move both radially inwards and then upwards into (e.g. a groove in) the implant, a more secure engagement with the implant can be provided.

In addition, as the engaging means are forced upwards into the implant, the first part, and preferably also a seal provided on the lid, e.g. on the first part, may be drawn down onto the implant, thereby compressing the seal. This may create a strong and safe seal between the implant and the lid, which can ideally withstand pressures from intestinal fluid, for example.

In a preferred embodiment, the first part is a cap. For example, the first part, or cap, may be substantially circular.

The cap may be formed of a circular top part and a ring-shaped side part.

The cap, and preferably its top part, may comprise one or more grooves.

For example, the cap may comprise a first groove which preferably runs from one side of the top part, preferably across the centre of the top part, to the opposite side of the top part. A recess may be provided along one or both sides of the groove.

The cap may comprise a second groove provided, for example, in the base of the first groove. The base of the first groove may be otherwise flat. The second groove is preferably narrower than the first groove and preferably runs from one side of the top part, e.g. where the first groove starts, preferably across the centre of the top part, and preferably almost, but not quite, to the opposite side of the top part. The centrelines of the first and second grooves are preferably co-linear.

On the base of the second groove, and preferably spaced along its centreline, there may be provided one or more, preferably two upwardly-projecting bumps. The one or more bumps preferably do not project any higher than the depth of the second groove, such that they do not project up into the first groove.

The side part of the cap preferably projects downwards from the circumferential edge of the top part.

Within the cap and preferably on an outer surface of the side part, there may be provided one or more, preferably three, preferably identical and preferably equally circumferentially spaced apart, grooves or recesses. Each groove or recess may comprise an upwardly-extending part or a circumferentially-extending part, and preferably both an upwardly-extending part and a circumferentially-extending part. The upwardly-extending part may extend upwards from the bottom of the side part towards, but not as far as, the top part. The groove may then continue in a circumferentially-extending part from the top of the upwardly-extending part circumferentially around the side part. Preferably, each groove does not extend as far around the side part as the next groove so that a gap without any groove is present between the grooves.

The upwardly-extending part of each groove may be shallower than the circumferentially-extending part. Thus, there may be a small step "down" (or radially inwards with respect to the cap) from the upwardly-extending part to the circumferentially-extending part, which may start just above it.

In addition, or alternatively, there is preferably a (relatively small) ridge or bump provided along or at a top end of the upwardly-extending part before the circumferentially-extending part.

In the circumferentially-extending part of each groove there may be a (relatively thin) ridge, preferably along most but not the entire length of the centreline of the circumferentially-extending part. The ridge preferably does not extend as far as either end of the circumferentially-extending part.

Preferably, as each circumferentially-extending part extends around the side part, it also extends slightly upwardly, such that each circumferentially-extending part preferably slopes upwards around the side part.

Preferably, on the underside of the top part, and e.g. inside the side part, there is a radially inner groove and/or a radially outer groove. The radially outer groove may be bounded or formed by the radially inner surface of the side part and a first circular wall. The radial inner groove may be bounded or formed by the first circular wall and a second circular wall.

Preferably, the second part is a base, the base being preferably substantially ring-shaped, e.g. with a substantially circular opening in its centre.

For example, the base may comprise a side part and, for example, a radially inwardly extending part which may extend radially inwardly from a lower (in use) circumferential edge of the side part. The radially inwardly extending part may form or comprise, e.g. at its centre, the substantially circular opening of the base.

On the outer surface of the side part or base there are preferably gripping regions with, e.g., ridges to facilitate gripping of the base, e.g. for rotation and/or when placing it over an implant.

Preferably, the base has a rounded or curved bottom, e.g. where the side part joins the radially inwardly extending part. Alternatively or additionally, the lid (e.g. its base) and/or the implant is/are dimensioned such that when the lid is attached to an implant there is a small gap between the patient's skin and the bottom of the lid/base. This means that there would be little or no abrasion on a patient's skin, e.g. when sitting or bending.

The base is preferably dimensioned so that the first part or cap can fit inside it, preferably exactly. In other words, an inner diameter of the base is preferably equal to an outer diameter of the first part or cap.

On the upper or inner surface of the base or, preferably, its radially inwardly extending part, there is preferably a, e.g. circumferential, groove which may be formed by the inner surface of the side part and a circular ridge, for example, e.g.

extending upwardly from, e.g., the inner circumference of the inwardly extending part. The ridge is preferably dimensioned so as to fit in a (e.g. radially outer) groove of the first part or cap when the lid is assembled.

At one or more, preferably three, preferably equally, circumferentially spaced apart positions along the circumferential groove there are, for example, one or more recesses or straight grooves, which may be slightly deeper than the circumferential groove. The one or more recesses or straight grooves are preferably arranged and dimensioned such that they can hold, support or contain the engagement means.

Above, e.g. the centre point of, each of these recesses or straight grooves, and extending from, e.g., the inner surface of the side part, there may be one or more, preferably three, preferably circular guide projections. The one or more guide projections are preferably dimensioned so as to fit in, and slide along, a groove provided in the cap or first part.

Associate with each recess or straight groove, for example at either end of each straight groove, preferably on a radially inner side, there may be provided a resilient tongue which can, for example, act as a weak spring (e.g. against the engagement means in each recess or straight groove).

A recess is preferably provided in the side part above one of the guide projections. The recess is preferably dimensioned such that a slider (described below) may fit or be slid through it.

The lid preferably comprises means for providing tactile feedback to a user indicating when the lid is in an engaged and/or disengaged state. For example, the ends of the recess in the side part may such tactile feedback when a part of a slider, or other rotation means (see below), for example, abuts against them (e.g. following rotation of the slider/base).

Preferably, the first part is or can be snap fitted into the second part. This is an easy and secure way to assemble the two parts whilst still ensuring that they can rotate with respect to each other.

Preferably, the first and second parts comprise complementary guide means, or guiding parts, for example to facilitate their relative rotation.

One part (e.g. first or second part) may comprise a projection and the other part a groove for guiding the projection.

For example, the complementary guide means may comprise one or more grooves provided on the first part or the second part, and one or more complementary protruding parts or projections provided on the other of the first part and the second part, whereby the one or more protruding parts are arranged to extend into the one or more grooves, thereby allowing the first and second parts to rotate relative to each other.

Preferably, the first and second parts are arranged such that as the second part is rotated relative to the first part (or vice versa), the first part is also made to move (e.g. by complementary guide means) axially with respect to the second part. As such, as the first part is rotated with respect to the second part, the first part may be made to move towards or away from, or into or out of, the second part, depending on the direction of rotation.

The first part may comprise or have connected thereto a rotation means (or anvil) for facilitating rotation of the second part relative to the first part (or vice versa). For example, the rotation means may protrude from, or be able to protrude from, the first part to facilitate rotation of the second part, e.g. by holding the first part stationary. Alternatively, the rotation means could be used to facilitate rotation of the first part, whilst the second part is held stationary.

Although the term "rotation means" is used, it will be appreciated that the rotation means itself need not necessarily rotate, it may merely facilitate rotation of another part. Thus, in this application, "rotation means" should be interpreted as a means for facilitating rotation of the second or first part (or "rotation facilitation means"), which need not itself necessarily be rotated. Indeed, in a preferred form of use, the rotation means is held stationary and used as a kind of "anvil" or holding means. For example, the rotation means may be, and preferably is, used to hold the first part stationary whilst the second part is rotated with respect to the first part. However, alternatively, the rotation means could be used to rotate the first part with respect to the (stationary) second part.

The rotation means is preferably retractable between a first position in which the second part may be rotated relative to the first part (or vice versa) (the lid is "unlocked"), and a second position in which the second part may not be rotated relative to the first part (or vice versa) (the lid is "locked"). Thus, when the rotation means is in the second (locked) position, inadvertent rotation of the first part may be prevented.

The rotation means may, for example, be a slider arranged to slide, preferably radially, in a groove, for example, provided in the first part.

The rotation means is preferably dimensioned so as to extend across a diameter of the first part.

In a preferred embodiment, the rotation means is substantially rectangular but may have curved ends, e.g. to match or correspond to the circumference of the first part.

The rotation means preferably has a curved upper surface with, for example, the curvature of this surface extending along the length of the rotation means.

On a bottom surface of the rotation means and, for example, towards one end, there may be provided one or more, preferably two, preferably parallel ridges, e.g. of equal length and preferably extending along a (relatively short) length of the rotation means.

Additionally or alternatively, a bump is preferably provided on the bottom surface of the rotation means. For example, the bump may be provided in a region between two ridges and the bump may extend between the two ridges. The bump is preferably curved. The ridges preferably extend slightly further along the length of the rotation means than the bump.

The lid preferably comprises means for providing tactile and/or audible feedback (preferably both) (e.g. tactile and/or audible feedback part(s)) to a user for indicating when the lid is in locked/unlocked states/positions. For example, interaction between one or more bumps, ridges or grooves provided on the rotation means and/or first part (e.g. in a groove in the first part) may provide such feedback. Preferably, the bump and/or one or more ridges provided under the rotation means, and/or the one or more upwardly-projecting bumps and/or an end of the second groove on the first part, are arranged such that interaction between them many provide such feedback.

A preferably curved groove is provided on the bottom surface of the rotation means, e.g. around its longitudinal mid-point. The curved groove preferably extends from one edge of the rotation means towards, but preferably not as far as, the opposite edge. The curved groove preferably has a radius of curvature on its inner edge corresponding to that of the outer circumference of the first part, or the inner circumference of the top of the second part.

On preferably the upper surface of the rotation means, e.g. at one end, there may be provided a marking or sign such as a single or double-ended arrow, showing, for example, the direction(s) in which the rotation means is to be moved or slid, in use.

The rotation means may comprise, e.g. at an (other) end of e.g. its upper surface, a gripping area, with one or more ridges or other gripping means, e.g. for facilitating the moving or sliding of the rotation means, in use.

Along one or preferably both edges of the rotation means, e.g. from its bottom side, there may be provided one or more projecting parts. One projecting part may be broken, or have a gap, at one point, e.g. where it extends over a curved groove provided on the bottom surface of the rotation means. The projecting part(s) is/are preferably dimensioned so as to fit in recesses present inside a groove provided in the first part.

As described above, the rotation means may, in addition to providing a means for rotating the second (or first) part, provide a means for locking/unlocking the lid (a locking means). However, it is also possible for a locking means to be provided separately from, and in addition to, the rotation means, e.g. as a separate part.

Thus, in some embodiments, the lid may comprise locking means for locking/unlocking the lid. Preferably, the locking means is movable between a first position in which the first part may be rotated relative to the second part (the lid is "unlocked"), and a second position in which the first part may not be rotated relative to the second part (the lid is "locked"). Thus, when the locking means is in the second (locked) position, inadvertent rotation of the first part may be prevented.

The locking means could be any kind of locking part capable of allowing/preventing rotation of the second part relative to the first part (or vice versa). For example, the locking means could comprise a retractable member (e.g. a pin or slider) which can be moved between a first, e.g. inserted, position, in which rotation of the second part relative to the first part (or vice versa) is prevented (the lid is locked), and a second, e.g. retracted, position, in which rotation of the second part relative to the first part (or vice versa) is possible (the lid is unlocked). For example, in its first position, the retractable member could extend, e.g. in an axial direction, through the first part into a hole or recess in the second part, thereby preventing their relative rotation and locking the lid.

Preferably, the locking means is arranged such that, when the lid is positioned on an implant, the locking means can only be moved from its unlocked to its locked position when the lid is properly engaged with the implant. Thus, when the lid is not properly engaged, the lid is prevented from being locked. This can help to prevent improper positioning of the lid on an implant, which could result in leakage.

The lid preferably further comprises a seal, e.g. for providing sealing engagement with the implant. The seal may be provided in or be part of the first part.

For example, the seal may be a sealing ring, e.g. provided in a preferably circular groove in the first part.

Alternatively, the seal, e.g. a sealing ring, may be injection moulded into the first part. This could be done by first moulding the first part, e.g. in a moulding tool, and then removing an insert from the tool such that sealing material (i.e. material for forming the seal) can then be moulded directly onto the first part (or the first part could be moved to a second chamber in the moulding tool, shaped such that the sealing material will form a seal when moulded into place on the first part).

The sealing ring is preferably circular and dimensioned so as to fit in a radially inner groove in the first part. The sealing ring preferably has a flat side and a curved side, and is preferably positioned in the first part with its flat side facing towards the bottom of the radially inner groove (i.e. upwards, in use). One or more, preferably two, small projections may be provided, e.g. opposite each other, on the sealing ring, and may extend e.g. perpendicularly from the flat side of the ring.

Other forms of seal could also be used.

Preferably, as the second part is rotated with respect to the first part (or vice versa), the seal can be made to move towards and to press against a surface of the implant, e.g. by relative axial movement of the first part.

Thus, the lid preferably comprises a dual locking mechanism, e.g. as the second part is rotated with respect to the first part (or vice versa) the engaging means engage with the implant and the seal is compressed against the implant. Once engaged and sealed in this way, the lid can preferably be locked (e.g. by placing the rotation means in a locked position) in a position in which the engaging means cannot disengage from the implant and/or the seal cannot become decompressed. The lid, e.g. the first part, preferably comprises one or more visual signs or indicators to show at what position the lid is in an open/closed/locked/unlocked position, for example.

The lid may be made of plastic metal, wood, a combination material, a composite material and/or rubber. Preferably, the lid is preferably made of plastic, e.g. polypropylene or silicone.

Preferably, the first and second parts of the lid are made of different materials, e.g. different kinds of plastic. This is because some (e.g. plastic) materials can tend to stick to each other when under some pressure. Thus, to minimise the possibility of this kind of friction occurring between the first and second parts, it is preferred that they are made from different materials.

The engaging means may be made or metal, e.g. stainless steel, fibre, hardwood, a soft metal, or plastic, for example.

However, preferably the engaging means is made of a softer material than that of the (e.g. titanium) implant. This can help to ensure that the engaging means wears out before the edge of a groove in the implant, for example, (or other receiving part for the engaging means) over which the engaging means moves.

For example, the engaging means could be made of a plastic/polymeric and possibly fibre-reinforced material.

Preferably, the engaging means, and all parts of the lid, are made of non-magnetic materials (e.g. aluminium, brass) for MRI compatibility.

The seal is preferably made of a medical grade soft polymer.

The lid may be cleaned with normal household methods, e.g. including one or more of rinsing, detergent, soap, boiling, bleaching and alcohol.

The present invention also relates to an implant with a lid as described above or below attached thereto.

The present invention also relates to a method of manufacturing a lid for a medical implant, e.g. as described above, the method comprising: providing a first part, a second part and engaging means; and assembling the first part, the second part and the engaging means to form a lid such that the first part is rotatable relative to the second part and, in use, rotation of the first part relative to the second part causes the engaging means to engage with and attach the lid to the implant. The first part, second part and/or engaging means are preferably as described above.

The method of manufacturing a lid may comprise one or more of the following steps:
  providing, inserting or locating the engaging means in the second part;
  providing, inserting or locating a seal, e.g. as described above, in the first part;
  providing, inserting or locating a rotation means, e.g. as described above in the first part.

These steps may be performed in any order and/or in parallel with one or more of each other.

The method may alternatively or additionally comprise (e.g. preferably after the above steps) inserting or locating the first part (with seal and/or rotation means, if provided) in the second part (e.g. with engaging means).

The first part may then be rotated with respect to the second part.

The rotation means may, for example, be inserted or slid into e.g. a groove in the first part.

In a preferred method, the second part is placed with a radially inwardly extending part located at the bottom. Engaging means, e.g. one or more, preferably three, pins, is/are then preferably placed in the second part, e.g. in each of (three) preferably straight grooves.

The first part is preferably placed with a groove, e.g. a radially inner groove, facing upwards. The seal is then preferably placed into the groove, e.g. with a flat side facing downwards into the groove.

The first part is preferably placed e.g. with an upper surface facing upwards. The rotation means may be inserted into or connected to the first part, e.g. by sliding or inserting the rotation means into a groove or recess in the first part.

As the rotation means is slid into the first part, resistance may be felt as a e.g. curved bump provided under the rotation means (e.g. as described above) meets one or more bumps on the first part (e.g. as described above). Some additional force may therefore be required to cause the e.g. curved bump to pass over the one or more bumps on the first part.

After the rotation means has been inserted into the first part, the bump on the ends of one or more ridges on the rotation means (e.g. as described above) may abut against a closed end of a groove in the first part (e.g. as described above) and the rotation means may be prevented from being inserted any further into or across the first part.

The one or more ridges and the closed end of the groove are preferably positioned such that at this point, i.e. when the one or more ridges abut against the closed end of groove, a curved groove (e.g. as described above) on the underside of the rotation means is positioned such that it extends around the outer circumference of the first part.

The rotation means should preferably be moved or slid into this position, i.e. as described above, before further steps of assembly of the lid described below are performed.

The assembled first part (e.g. with a rotation means and/or seal as described above) is preferably inserted into or placed around the assembled second part (e.g. with the engaging means, as described above).

In order to do this, the assembled first part is preferably positioned with its upper surface facing upwards, and the assembled second part is preferably positioned, for example on a level surface, with a radially inwardly extending part (e.g. as described above) located at the bottom or facing downwards. The first part is further preferably positioned such that one or more walls or boundaries of one or more grooves in the first part, e.g. one or more upwardly-extending parts of grooves in the first part, are each located directly above a guide, e.g. a preferably circular guide projection, e.g. as described above, provided in the second part.

The assembled first part is further preferably positioned such that its engaging means (if provided) slightly overlaps a recess in a side part of the second part (e.g. as described above).

The assembled first part and the assembled second part are, e.g. after the above alignment procedure, preferably pressed or snapped together, e.g. by pressing the first part into or over the second part, such that, for example guides provided in the second part pass over, for example, ridges provided e.g. at a top end of each upwardly-extending part, and, preferably, then into circumferentially-extending parts.

As the assembled first part has preferably been positioned such that the engaging means slightly overlaps a recess in a side part of the second part, part of a top edge of the second part may be fitted into the curved groove on the underside of the engaging means, if provided.

Next, the assembled first part is preferably rotated, e.g. clockwise when viewed from above, with respect to the second part, (or vice versa), by, for example, pushing or pulling or otherwise moving the rotation means. By moving the rotation means in this way, the first part is preferably rotated as far as it can be, e.g. until the guides in the second part reach upper ends (e.g. of circumferentially-extending parts) of grooves in the first part (e.g. opposite to the ends where the circumferentially-extending parts meet the upwardly-extending parts) and may thus be prevented from moving further.

As the first part is rotated in this way, it is also preferably drawn (further) down into or onto the second part, e.g. due to a slope of grooves in the first part.

When the first part has been rotated as far as it can be, e.g. when the guides in the second part reach ends of grooves in the first part, the rotation means is preferably located inside the recess in the side of the second part.

Next, the rotation means is preferably pushed inwards, e.g. through the recess and/or a groove in the first part, until, for example, the rotation means is prevented from moving further, e.g. by abutting against a side part of the second part. At this point, the rotation means is preferably positioned across the (e.g. entire) diameter of the lid, within, for example, a groove on the first part.

The rotation means is, at this point, preferably flush with the surrounding area of the first part.

In addition or alternatively, the longitudinal length of the rotation means is preferably equal to an outer diameter of the second part such that, at this point, the rotation means does not project outwardly from base.

This means that the lid provides a relatively smooth and continuous outer surface, which would not, for example, get caught on clothing or other objects which could apply a force against it and potentially damage the tissue-implant junction. It also means that the lid is discrete for a user.

Once the lid has been assembled, e.g. in the above way, it may be provided e.g. to a patient or other user, for fitting onto e.g. an implant.

The present invention also relates to a method of attaching a lid for a medical implant, e.g. as described above, to an implant, the lid comprising a first part, a second part and engaging means, wherein the method comprises: placing the lid over a protruding end of the implant and then rotating the second part relative to the first part (or vice versa), such that the engaging means engages with and attaches the lid to the implant. The first part, the second part and/or the engaging means are preferably as described above.

The method preferably first comprises extending (e.g. sliding) a rotation means (e.g. as described above) from the first part, such that the rotation means may be used to rotate the first part. For example, starting from a lid with rotation means inserted in or across the first part, before the lid is fitted on an implant, the rotation means may be extended or slid outwardly, e.g. along a groove in first part.

The first part may be rotated, e.g. anti-clockwise with respect to the second part when viewed from above, such that the first part preferably rises up out of the second part slightly. At this point, the rotation means may, for example, be only slightly overlapping (or not overlapping at all) a recess in the second part (e.g. as described above).

The lid may then be ready to be fitted onto an implant.

A user preferably holds a projecting end of the rotation means and may place the lid over an exterior section of the implant.

The second part is then preferably rotated, e.g. by pushing/pulling/moving the rotation means, for example in an anti-clockwise direction with respect to the first part when view from above (or vice versa) until, for example, the rotation means is positioned completely in a recess in the second part (e.g. as described above).

As the second part is rotated with respect to the first part (or vice versa), the first part is preferably drawn down into or onto the second part, for example by virtue of one or more guides in the second part (e.g. as described above) being made to slide along grooves, for example, in the first part (e.g. as described above).

As the first part is drawn down into or onto the second part in this way, a side part of the first part preferably moves down, e.g. into a groove inside the second part, and forces the engaging means to engage with the implant.

The second part preferably comprises one or more resilient tongues arranged for pressing against the engaging means.

Preferably, the engaging means may be forced, e.g. by a part of the first part as it moves down into or onto the second part, radially inwardly, preferably against the one or more resilient tongues, and preferably slightly upwardly into a groove or other recess in the implant, e.g. a groove around an exterior circumference of an exterior section of the implant.

This engaging of the engaging means with the implant can secure and hold the lid onto the implant and, for example, prevent users, clothing or other objects, from being able to simply move or pull the lid straight off of the implant, e.g. unintentionally.

In addition, as the first part is drawn down into or onto the second part, a seal (e.g. as described above), provided for example on an underside of the first part, may be compressed against the implant, e.g. against an upper surface of an exterior section of the implant, thereby forming a leak-proof seal between the implant and the lid.

Once the lid has been attached to the implant, the rotation means is preferably slid or moved back to its unextended position, e.g. back across the lid, e.g. through and into a groove on the first part. Thus, once the lid has been attached to an implant, the rotation means may be retracted such that it is no longer protrudes from the lid.

The present invention also relates to a method of removing a lid for a medical implant, e.g. as described above, from an implant, the lid comprising a first part, a second part, and engaging means, wherein the method comprises: rotating the second part relative to the first part (or vice versa) such that the engaging means disengages from the implant, and then removing the lid from the implant. The first part, the second part and/or the engaging means are preferably as described above.

In order to remove a lid from an implant, the reverse procedure to that described above may be performed.

For example, the lid may start with a rotation means in a retracted or non-extended position with respect to the rest of the lid. The rotation means may then be extended, e.g. pulled outwards for example through a groove in the first part. When extended, for example, the rotation means may be used to rotate the second part, e.g. in a clockwise direction, with respect to the second part (or vice versa). This rotation preferably causes the first part to move upwards and slightly out/off of the second part, such that, for example, a part (e.g. a side part) of the first part no longer forces or holds the engaging means in engagement with the implant. The one or more resilient tongues, for example, preferably cause the engaging means to be retracted from the implant, e.g. from a groove in the implant. At this point, as the first part has moved upwards slightly, a seal is preferably no longer compressed against the implant.

The user may then lift the lid off of the implant, e.g. with little or no resistance.

After removal of a lid from an implant, it should preferably be washed.

The concept of a lid with a locking means is viewed as inventive in its own right and thus, viewed from a further aspect, there is provided a lid for a medical implant, the lid comprising engaging means and locking means, wherein the locking means are movable between a locked position, in which the engaging means may not engage with/disengage from an implant, and an unlocked position, in which the engaging means may engage with/disengage from an implant.

Thus, when the locking means is in the locked position (i.e. the lid is locked), the lid may not be, e.g. accidently, disengaged from an implant and accidental removal of the lid from an implant may be prevented. Conversely, when the locking means is in the unlocked position (i.e. the lid is unlocked), the lid may be engaged with/disengaged from the implant. Thus, the lid may be locked onto an implant in its engaged state, and a conscious and active step must be taken such that the lid may be unlocked and then disengaged from the implant.

The locking means could be or comprise a locking part suitable for locking/unlocking the lid, and preferably also engaging/disengaging the engaging means.

The phrase "locking the lid" means putting the lid into a locked state wherein its engaging means cannot be engaged with/disengaged from an implant. Conversely, the phrase "unlocking the lid" means putting the lid into an unlocked state wherein its engaging means can be engaged with/disengaged from an implant.

The locking means could, for example, be the rotation means as described above.

Alternatively, the locking means could be any kind of locking part capable of allowing/preventing rotation of the second part relative to the first part (or vice versa). For example, the locking means could comprise a retractable member (e.g. a pin or slider) which can be moved between a first, e.g. inserted, position, in which rotation of the second part relative to the first part (or vice versa) is prevented, and a second, e.g. retracted, position, in which rotation of the second part relative to the first part (or vice versa) is possible. For example, in its first position, the retractable member could extend, e.g. in an axial direction, through the first part into a hole or recess in the second part, thereby preventing their relative rotation.

The lid may comprise any or all of the other features described above or below.

Viewed from a further aspect, there is provided a method of locking a lid for a medical implant, the lid comprising engaging means and locking means, the method comprising moving the locking means into a locked position in which the engaging means may not engage with/disengage from an implant. The lid may be as described above or below, and the method may comprise any of the further features described above or below.

Viewed from a further aspect, there is provided a method of unlocking a lid for a medical implant, the lid comprising engaging means and locking means, the method comprising moving the locking means into an unlocked position in which the engaging means may engage with/disengage from an implant. The lid may be as described above or below, and the method may comprise any of the further features described above or below.

The concept of a lid with compression means that can be used to draw the lid down onto an implant is also viewed as inventive in its own right and thus, viewed from a further aspect, there is provided a lid for a medical implant, the lid comprising a seal and compression means, wherein the compression means is arranged such that, when the lid is placed over an implant, activation or use of the compression means causes at least the seal to move down towards the implant such that the seal is compressed against the implant.

As such, the compression means can be used to cause the seal to move down onto the implant, such that the seal is compressed into preferably sealing engagement with the implant, thereby provided a leak-proof seal.

The seal (e.g. as described above) is preferably provided on an underside of the lid.

The lid preferably also comprises engaging means, e.g. as described above. The compression means is preferably arranged such that activation of the compression means causes the engaging means to engage with the implant (as well as the lid and its seal to move down towards the implant such that the seal is compressed against the implant), for example as described above. Thus, the compression means can preferably be used to control both the attachment or engagement of the lid to an implant, as well as the sealing of the lid to an implant.

The compression means could be or comprise any kind of compression part, e.g. that is suitable for compressing the seal against the implant.

For example, and e.g. as described above, the compression means could be or comprise a rotation means which can be used to cause the lid (or a part of the lid) to rotate downwards onto the implant, thereby causing the seal to be compressed onto the implant. The compression means could, for example, be the rotation means as described above.

Alternatively or additionally, the compression means could comprise a pushbutton on, for example the top of, the lid, or one or more, preferably two, protruding parts/levers/buttons on, e.g. the side of, the lid to push/squeeze.

The engaging means could comprise one or more fixed parts and one or more movable parts.

For example, as a fixed part, the engaging means could comprise a fixed edge, ridge or other protrusion provided on the lid for engaging with a corresponding groove or indentation on the implant (or vice versa). The edge, ridge or other protrusion could, for example, be provided on or around a lower inner rim of the lid, e.g. its base. It could, for example, cover half or less than half (e.g. around a third or less, around a quarter or less) of an inner circumference of the lid.

As one or more movable parts the engaging means could comprise one or more levers, pins, hooks or other movable engaging means. The one or more movable parts could be distributed, preferably evenly, along the remaining circumference of the lid, i.e., that not covered by the fixed part(s).

In one embodiment, the lid could comprise a edge or ridge covering the in circumference along one quadrant of the lid and one or more, preferably two or three, levers, pins or hooks, distributed, preferably evenly, over the circumference of the remaining three quadrants.

With such a lid, the lid could be slid onto an implant, for example, to engage the fixed part(s) with the implant, and then the movable part(s) could be activated (e.g. by the compression means) to further engage with the implant, and, preferably, compressing a seal provided on the lid with the implant to ensure sealing engagement of the lid with the implant.

The lid may comprise any or all of the other features described above or below.

A method of sealing a lid for a medical implant with or to an implant, the lid comprising a seal and compression means, the method comprising placing the lid over the implant and activating or using the compression means to cause the seal to move down towards the implant such that the seal is compressed against the implant. The lid may be as described above or below, and the method may comprise any of the further features described above or below.

BRIEF DESCRIPTION OF THE DRAWINGS

Preferred embodiments of the present invention will now be shown by way of example only and with reference to the accompanying drawings, in which:

FIGS. 17(a)-(d) show steps for fitting a lid of FIG. 3 onto an implant;

FIGS. 18(a)-(e) show steps for removing a lid of FIG. 3 from an implant; and

DETAILED DESCRIPTION OF THE INVENTION

Figure 1:
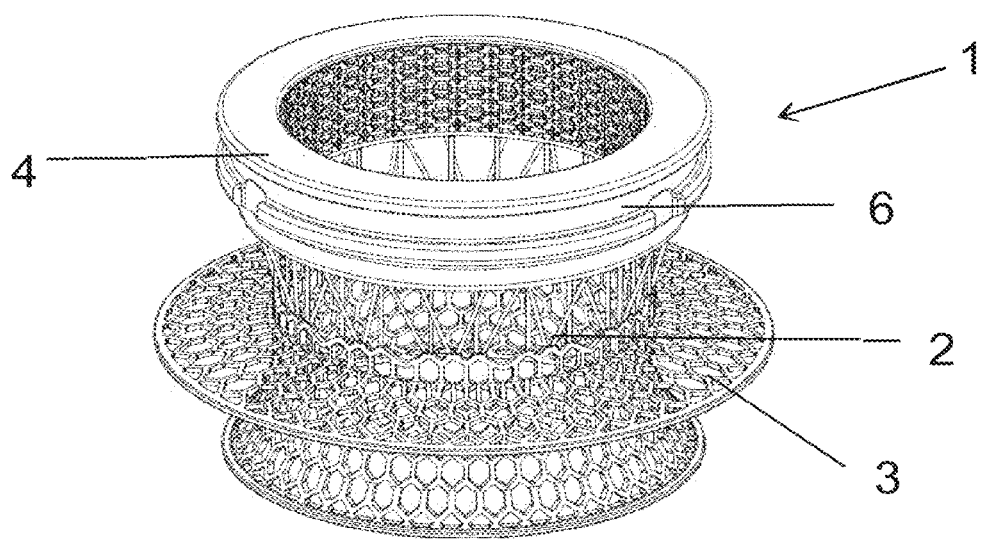
FIG. 1 shows a perspective view of an ostomy implant.
Figure 2:
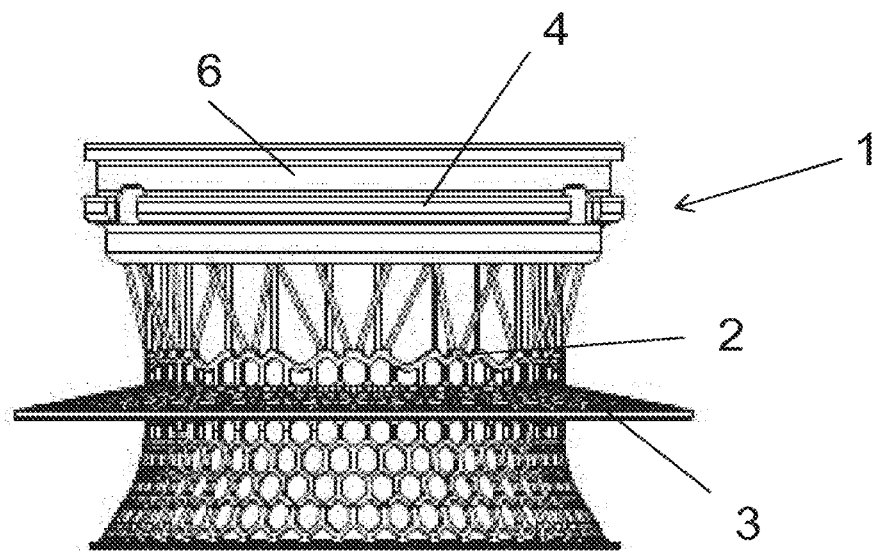
FIG. 2 shows a side view of the ostomy implant of FIG. 1.
Figure 3:
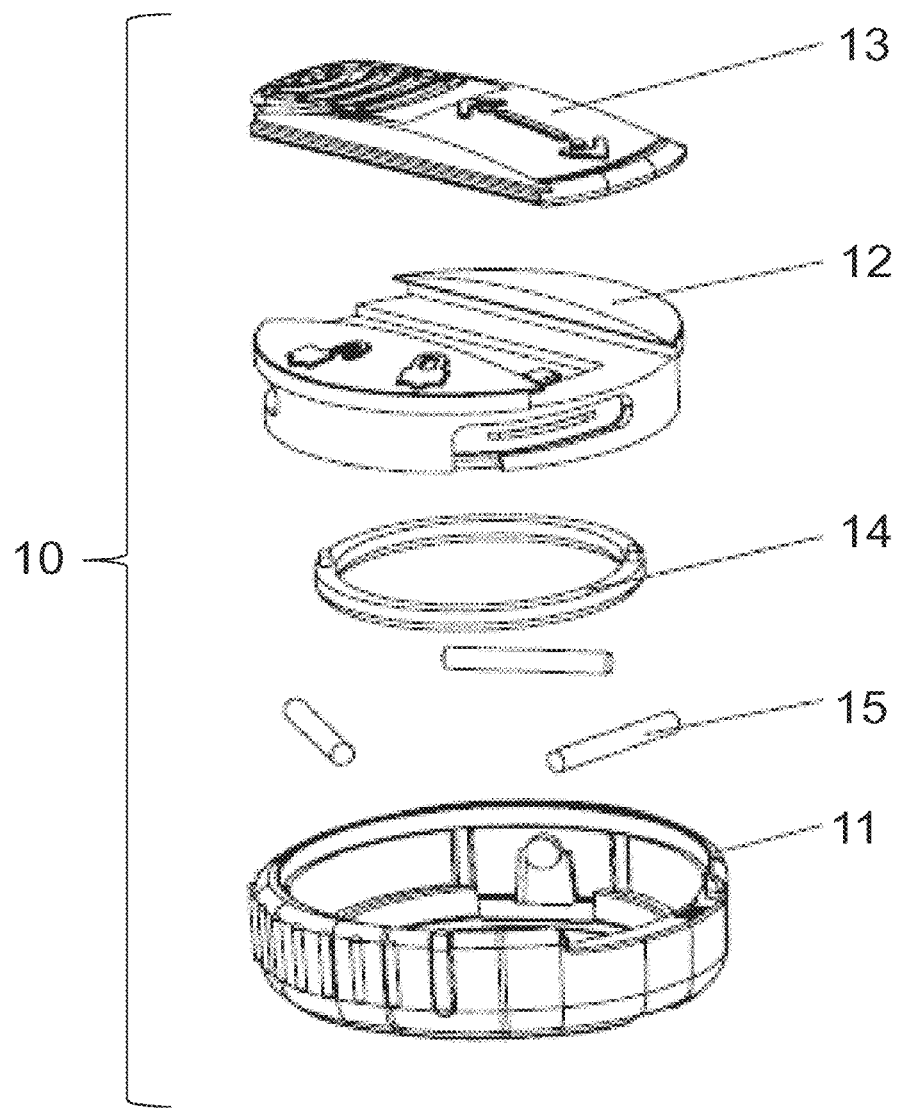
FIG. 3 shows an exploded perspective view of components of a lid according to an embodiment of the invention.

FIG. 3 shows an exploded perspective view of the components of a lid 10 according to an embodiment of the invention.

The components of the lid 10 consist of: a substantially ring-shaped base 11, a substantially circular cap 12, a slider 13, a sealing ring 14 and three pins 15. The respective components 11, 12, 13, 14, 15, of the lid 10 are described in more detail below.

Figure 4:
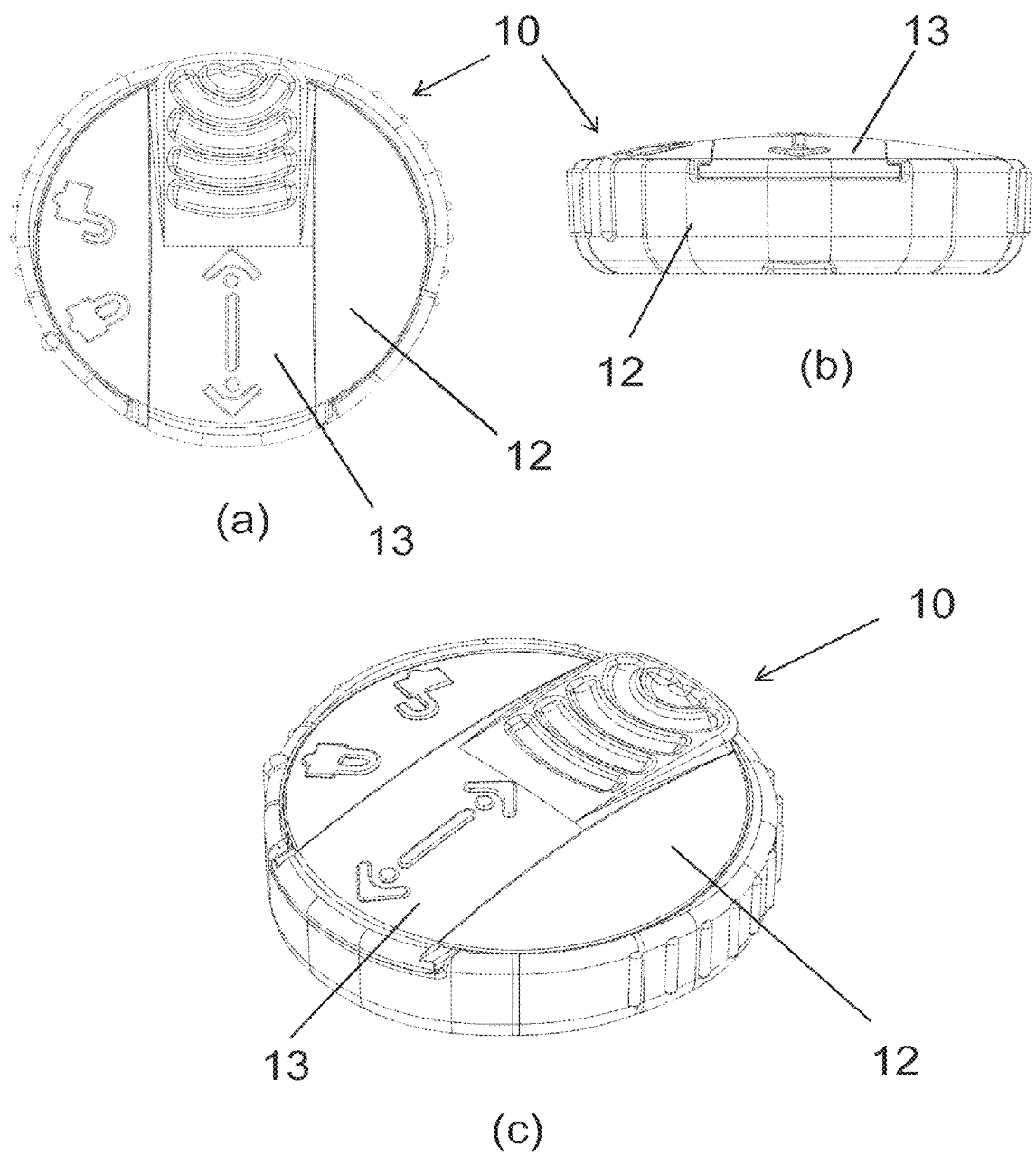
FIGS. 4(a)-(c) show a top, side and perspective view, respectively, of the lid shown in FIG. 3.
Figure 5:
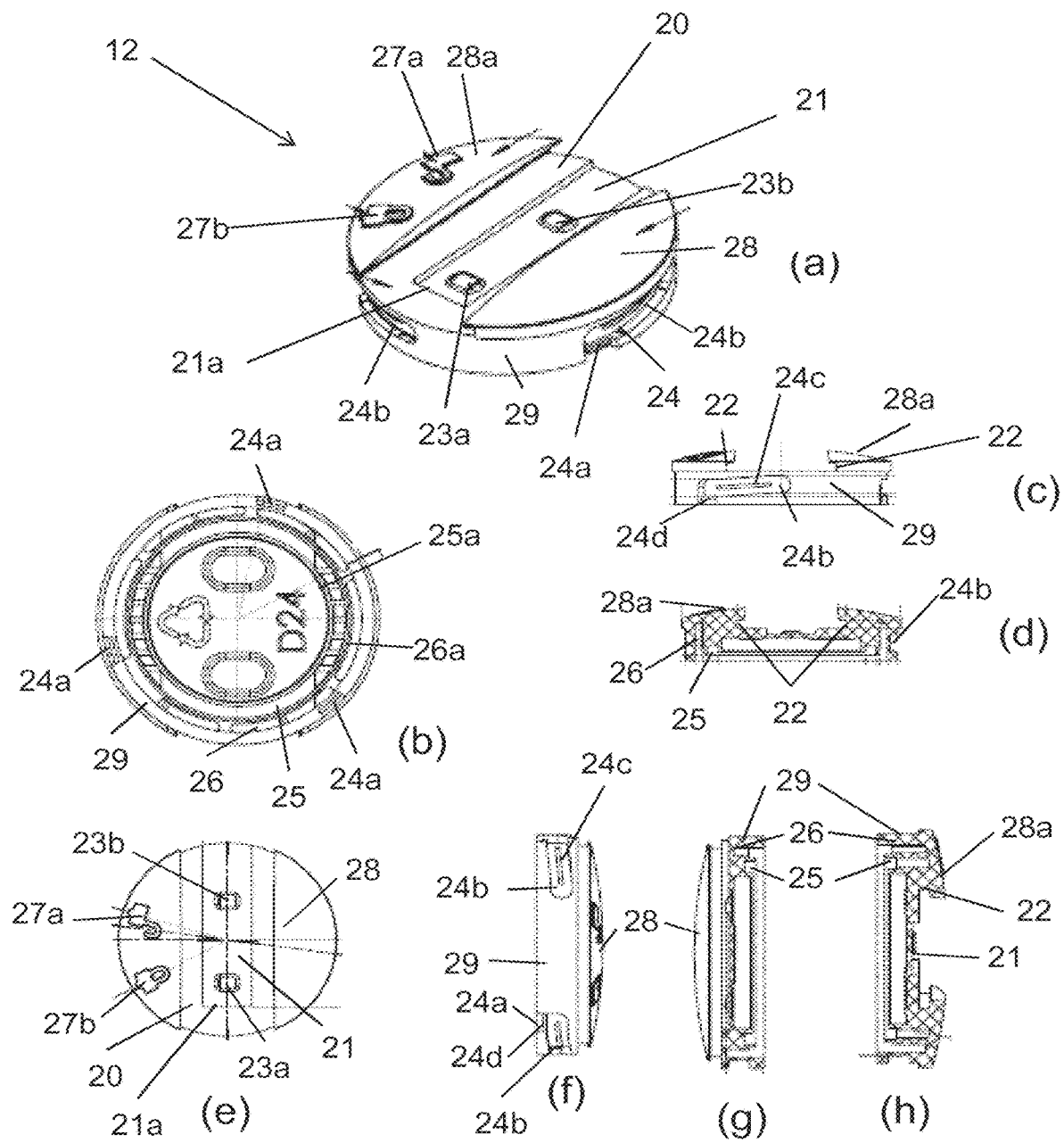
FIGS. 5(a)-(h) show a perspective, bottom, side, cross-sectional, top, side, cross-sectional and a further cross-sectional view, respectively, of the cap of the lid shown in FIG. 3.
Figure 6:
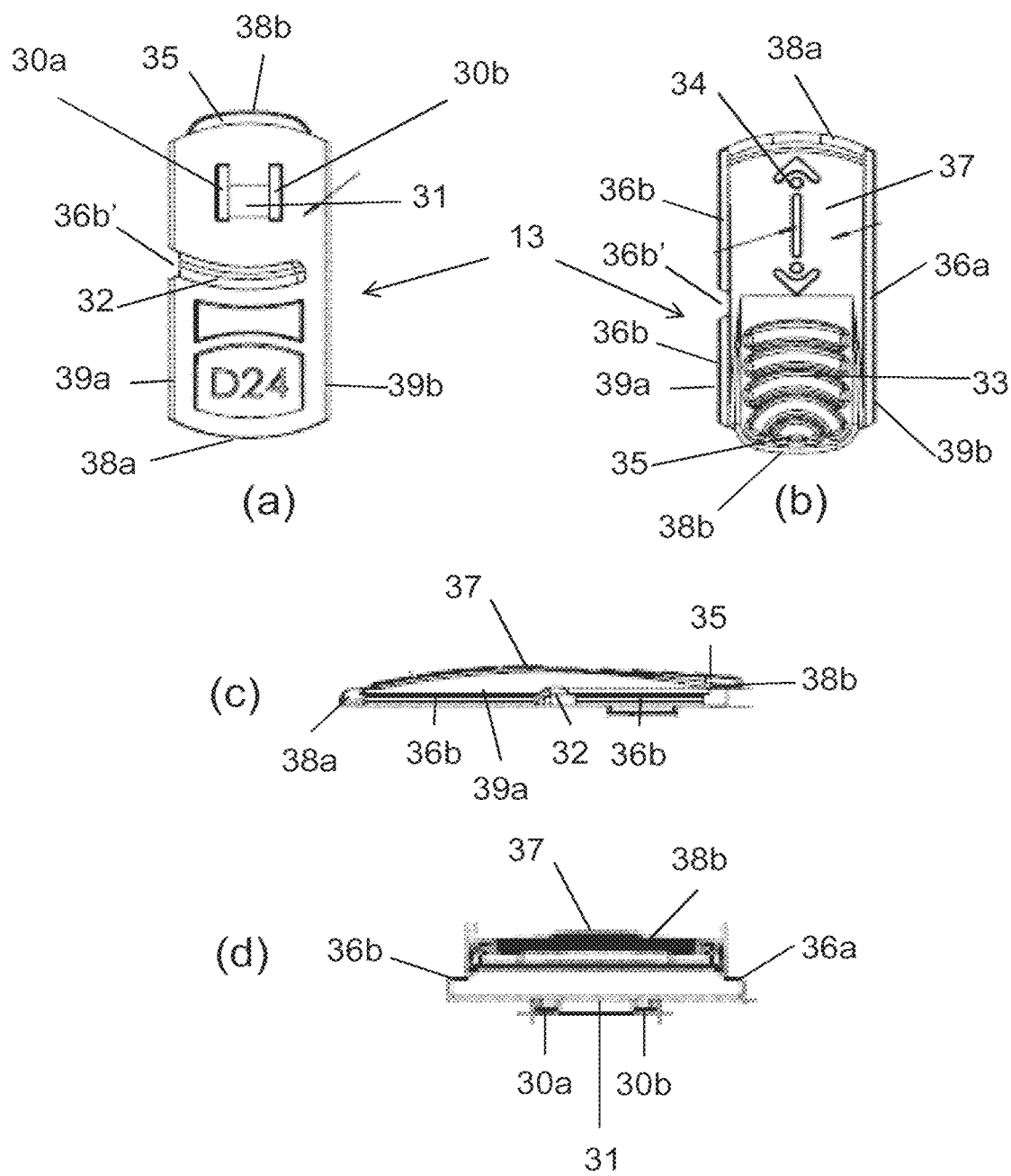
FIGS. 6(a)-(d) show a bottom, top, side and end view, respectively, of the slider of the lid shown in FIG. 3.
Figure 7:
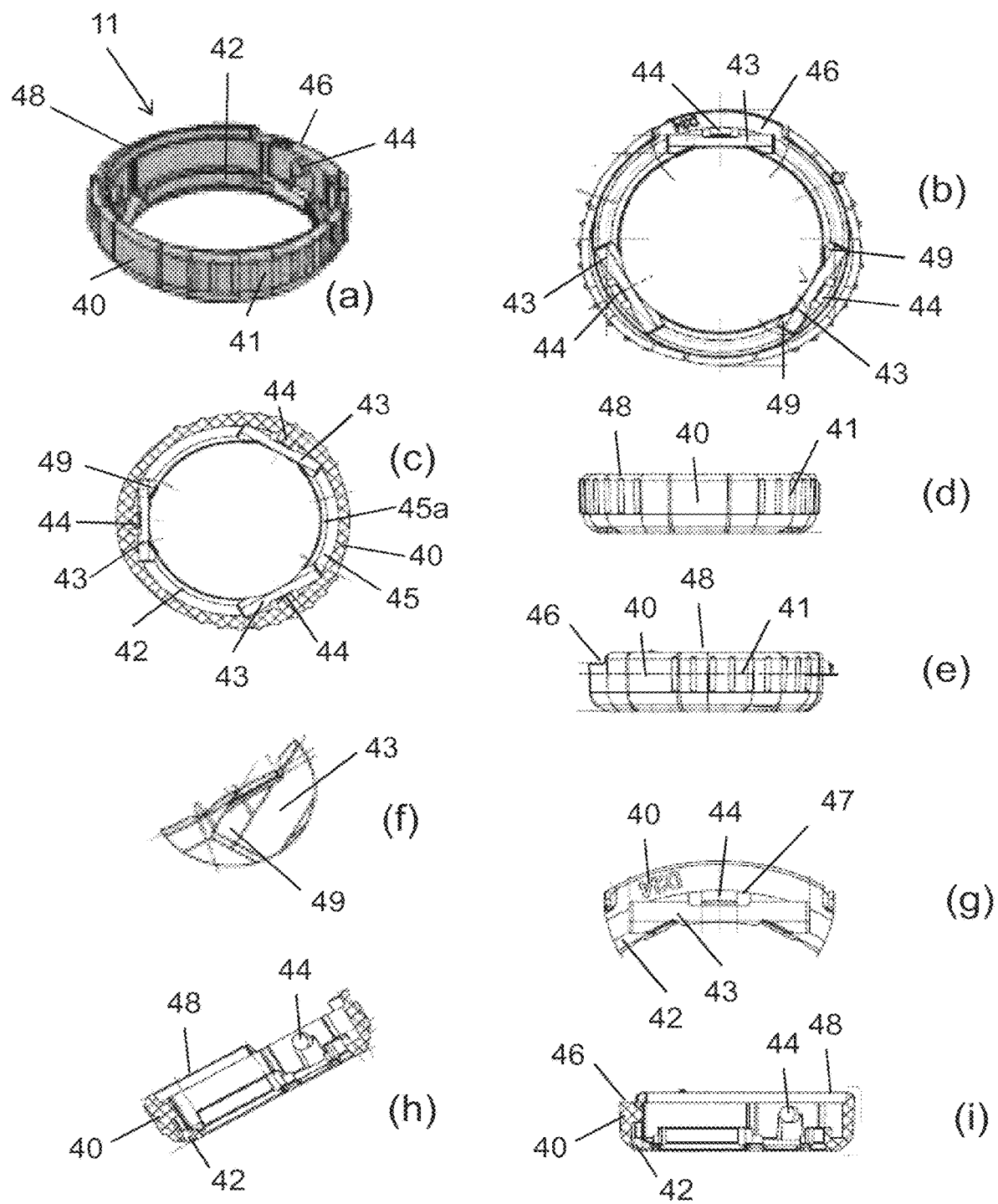
FIGS. 7(a)-(i) show a perspective, bottom, cross-sectional, side, further side, detail, further detail, further cross-sectional and further cross-sectional view, respectively, of the base of the lid shown in FIG. 3.

FIGS. 4(a)-(c) show top, side and perspective views, respectively, of the lid 10 of FIG. 3.

FIGS. 5(a)-(h) show a perspective, bottom, side, cross-sectional, top, side, cross-sectional and a further cross-sectional view, respectively, of the cap 12 of the lid 10 shown in FIG. 3.

The cap 12 is circular and is formed of a circular top part 28 and a ring-shaped side part 29.

In the top part 28 there is a first groove 20 which runs from one side of the top part 28, across the centre of the top part 28, to the opposite side of the top part 28. The upper surface 28a of the top part 28 slightly projects over the two sides of the first groove 20 forming a small recess 22 along either side of the groove 20.

Within the first groove 20, in its base (which is otherwise flat), there is a second groove 21. The second groove 21 is narrower than the first groove 20 and runs from the one side of the top part 28 where the first groove 20 starts, across the centre of the top part 28, and almost, but not quite, to the opposite side of the top part 28. The centrelines of the first and second grooves 20 and 21 are co-linear.

On the otherwise flat base of the second groove 21, and spaced along its centreline, there are two upwardly-projecting bumps 23a and 23b. The bumps 23a and 23b do not project any higher than the depth of the second groove 21, so they do not project up into the first groove 20. These bumps 23a and 23b are provided and positioned so as to give a definite "click" sound and feel feedback to the user, when the slider is pushed all the way into each of its two end positions. The "click" sound and feel feedback is provided as the bumps 23a and 23b pass over a corresponding bump 31 provided on the bottom surface of the slider 13 (see below).

On the upper surface 28a of the top part 28 there are two logos 27a and 27b marking locked and unlocked positions of the lid 10.

The side part 29 projects downwards from the circumferential edge of the top part 28.

Within the outer surface of the side part 29 are provided three identical and equally circumferentially spaced apart grooves 24. Each groove 24 consists of an upwardly-extending part 24a and a circumferentially-extending part 24b. The upwardly-extending part 24a extends upwards from the bottom of the side part 29 towards, but not as far as, the top part 28. The groove 24 then continues in the circumferentially-extending part 24b from the top of the upwardly-extending part 24a circumferentially around the side part 29. Each groove 24 does not extend as far around the side part 29 as the next groove 24 so that a gap without any groove is present between the grooves 24.

The upwardly-extending part 24a of each groove 24 is shallower than the circumferentially-extending part 24b of each groove 24. Thus, there is a small step "down" (or radially inwards with respect to the cap 12) from the upwardly-extending part 24a to the circumferentially-extending part 24b, which starts just above it. In addition, there is a small ridge 24d provided along the top end of the upwardly-extending part 24a before the drop "down" into the circumferentially-extending part 24b.

In the circumferentially-extending part 24b of each groove 24 there is a thin ridge 24c along most but not the entire length of the centreline of the circumferentially-extending part 24b. The ridge 24c does not extend as far as either end of the circumferentially-extending part 24b.

When the lid 10 is assembled, the three ridges 24c are in contact with three corresponding circular guide projections 44 located on the inside of the base part 11 (see below).

As each circumferentially-extending part 24b extends around the side part 29, it also extends slightly upwardly, such that each circumferentially-extending part 24b slopes upwards around the side part 29.

On the underside of the top part 28, and inside the side part 29, there is a radially inner groove 25 and a radially outer groove 26. The radial outer groove 26 is bounded or formed by the radially inner surface of the side part 29 and a first circular wall 26a. The radial inner groove 25 is bounded or formed by the first circular wall 26a and a second circular wall 25a.

FIGS. 6(a)-(d) show a bottom, top, side and end view, respectively, of the slider 13 of the lid 10 shown in FIG. 3.

The slider 13 is dimensioned so as to extend across a diameter of the lid 10, when assembled. As such, the slider 13 is substantially rectangular but has slightly curved ends 38a 38b to match the circumference of the lid 10. The slider 13 has a curved upper surface 37 with the curvature of this surface 37 extending along the length of the slider 13 (i.e. when assembled, across the diameter of the lid 10).

On the bottom surface of the slider 13 and towards one end 38b, there are two parallel ridges 30a, 30b of equal length extending along a short length of the slider 13. Extending between the two ridges 30a, 30b is a curved bump 31. The ridges 30a, 30b extend slightly further along the length of the slider 13 than the bump 31.

Around the mid-point of the slider 13, and on its bottom surface, is a curved groove 32 extending from one edge 39a of the slider 13 towards but not as far as the opposite edge 39b. The curved groove 32 has a radius of curvature on its inner edge corresponding to that of the outer circumference of the cap 12.

At one end of the upper surface 37 of the slider 13 there is marked a double-ended arrow 24, showing the directions in which the slider 13 is to be slid, in use. At the other end of the upper surface 37, there is a ridged area 33 with ridges for facilitating the sliding of the slider 13, in use.

Along each edge 39a, 39b of the slider 13, from its bottom side, there is a projecting part 36b, 36a, respectively. The projecting part 36b is broken, or has a gap 36b', at one point where it extends over the curved groove 32. The projecting parts 36a, 36b are dimensioned so as to fit in the recesses 22 present inside the first groove 20 of the cap 12.

FIGS. 7(a)-(i) show a perspective, bottom, cross-sectional, side, further side, detail, further detail, further cross-sectional and further cross-sectional view, respectively, of the base 11 of the lid 10 shown in FIG. 3

The base 11 is ring shaped and has a side part 40 and a radially inwardly extending part 42 which extends radially inwardly from a lower (in use) circumferential edge of the side part 40.

On the outer surface of the side part 40 there are gripping regions 41 with ridges to facilitate gripping of the base 11, for example in use, e.g. for rotating the base 11.

The base 11 is dimensioned so that the cap 12 can fit inside it exactly.

On the upper or inner surface of the radially inwardly extending part 42 there is a circumferential groove 45 formed by the inner surface of the side part 40 and a circular ridge 45a extending upwardly from the inner circumference of the inwardly extending part 42. The ridge 45a is dimensioned so as to fit in the radially outer groove 26 of the cap 12, when the lid 10 is assembled.

At three equally circumferentially spaced apart positions along the circumferential groove 45 there are three straight grooves 43 which are slightly deeper than the circumferential groove 45. Above the centre point of each of these straight grooves 43, and extending from the inner surface of the side part 40, there are three circular guide projections 44. These circular guide projections 44 are dimensioned so as to fit in, and slide along, the groove 24 of the cap.

These circular guide projections 44 are provided on short flexible arms and, as the base 11 or cap 12 is rotated, the guide projections 44 are arranged to travel over the ridges 24c provided in the grooves 24, as described above. As the guide projections move over the ridges 24c, this produces a slight breaking action to (or frictional force exerted against) the rotation between the cap 12 and the base 11, this provides a nice and solid "quality" feeling to a user of the lid. At the two rotational end positions, i.e. when the guide projections 44 are at either end of the grooves 24, the ridges 24c disappear and the breaking action does too, thereby creating distinct end positions, with the frictional force provided by the ridge 24c meaning that the cap 12 and the base 11 do not unintentionally rotate against each other.

In the radially inwardly extending part 42 beneath each circular guide projection 44, there is a rectangular hole 47. These holes 47 are not related to the function of the lid 10, but are present due to the injection moulding process used to make the lid 10. These holes 47 are needed for movable anvils in the injection moulding tooling to create the circular guide projections 44 described above.

At either end of each straight groove 43, on a radially inner side, there is a resilient tongue 49 which can act as a weak spring.

A recess 46 is provided in the side part 40 above one of the circular guide projections 44. The recess 46 is dimensioned such that the slider 13 can be slid through it.

Figure 8:
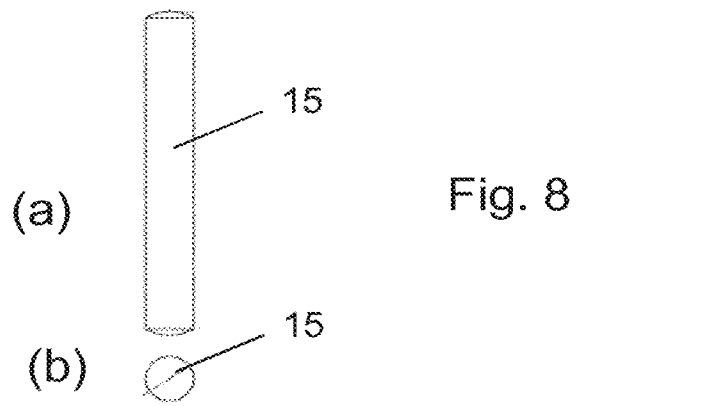
FIGS. 8(a) and (b) show side and end views, respectively, of a pin of the lid shown in FIG. 3.

FIGS. 8(a) and (b) show side and end views, respectively, of the pins 15 of the lid 10 shown in FIG. 3. The pins 15 are straight with a circular cross section and curved ends. Three pins 14 are provided for each lid 10 and they are dimensioned so as to fit in the three straight grooves 43 of the base 11.

Figure 9:
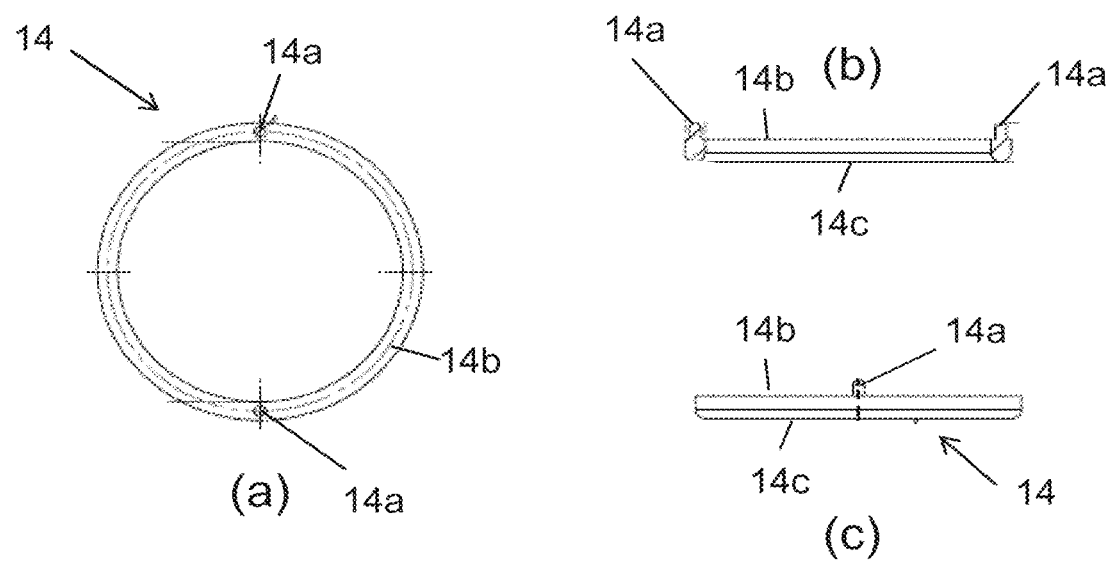
FIGS. 9(a)-(c) show a top, cross-sectional and side views, respectively, of the sealing ring of the lid shown in FIG. 3.

FIGS. 9(a)-(c) show a top, cross-sectional and side views, respectively, of the sealing ring 14 of the lid 10 shown in FIG. 3. The sealing ring 14 is circular and dimensioned so as to fit in the radially inner groove 25 of the cap 12. The ring 14 has a flat side 14b and a curved side 14c. Two small projections 14a are provided opposite each other on the sealing ring 14 and extend perpendicularly from the flat side 14b of the ring 14. The small projections 14a do not serve any purpose once the lid 10 is assembled but merely serve to identify the flat side 14b of the ring 14 more clearly, so that it can be inserted into the inner groove 25 of the cap 12 in the correct orientation.

Before the lid 10 is assembled from its component parts 11, 12, 13, 14, 15 and then packaged, it is cleaned and disinfected. The cleaning process includes ultrasonic cleaning-disinfection with 70% ethanol for 3-5 minutes. After this, and before assembly and packing, all parts 11, 12, 13, 14, 15 are dried by heat (maximum 70° C.) or in room air in a protected area to avoid condensation in the packaging. Cleaning is performed in a clean and controlled environment, in conjunction with assembly and packaging in sealable bags.

When the lids 10 are produced in volume, the lid parts 11, 12, 13, 14, 15 will be moulded in a clean-room environment directly. This means no cleaning (as described above) will be necessary before (or after) assembly.

The assembly process for the lid 10 will now be described.

FIGS. 10(a)-(c) show steps for inserting the three pins 15 into the base 11 for assembly of the lid 10.

First, as shown in FIG. 10(a), the base 11 is placed with its radially inwardly extending part 42 located at the bottom. A pin 15 is then placed in each of the three straight grooves 43, as shown in FIG. 10(b). The final configuration of the base 11 and pins 15 after performing these steps is shown in FIG. 10(c).

FIGS. 11(a)-(e) show steps for inserting the sealing ring 14 into the cap 12 for assembly of the lid 10.

First, cap 12 (as shown in FIG. 11(a)) is placed with its radially inner groove 25 facing upwards, as shown in FIG. 11(b). The sealing ring 14 is then placed into the radially inner groove 25 with its flat side 14b facing downwards into the groove 25, and its curved side 14c facing upwards out of the groove 25, as shown in FIGS. 11(c) and (d). The final configuration of the cap 12 and sealing ring 14 after performing these steps is shown in FIG. 11(e).

In an alternative embodiment, the cap 12 and sealing ring 14 are formed together using a two-step injection moulding process (forming first the cap 12 and then the sealing ring 14 on the cap 12) so that the method shown in FIGS. 11(a)-(e) is not required.

FIGS. 12(a)-(c) show steps for inserting the slider 13 into the cap 12 for assembly of the lid 10.

First, as shown in FIG. 12(a), the cap 12 is placed with its upper surface 28a facing upwards and the slider 13 is placed with its upper surface 37 facing upwards. The end 38a of the slider 13 is then slid into the first groove 20 of the cap 12 along axis L. The slider 13 is slid into the first groove 20 at the end of the first groove 20 where the second groove 21 extends to right to the circumferential edge of the cap 12. As the slider 13 is slid into the first groove 20, the projecting parts 36a, 36b of the slider 13 slide through the recesses 22 along either side of the groove 20.

As the slider 13 is slid through the first groove 20, resistance is felt as the curved bump 31 under the slider 13 meets the bumps 23b and then 23a in the second groove 21 of the cap 12. Some additional force is therefore required to cause the curved bump 31 to pass over the bumps 23b and then 23a in the second groove 21.

Figure 12:
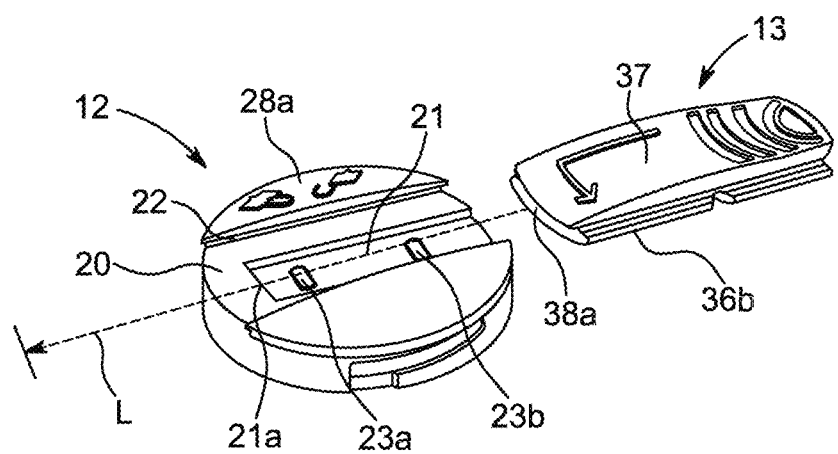
FIGS. 12(a)-(c) show steps for inserting the slider of FIG. 6 into the cap of FIG. 5.
Figure 12:
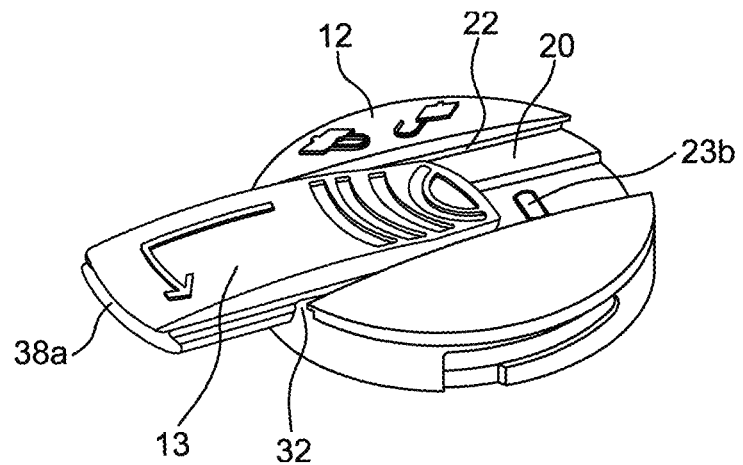
Figure 12:
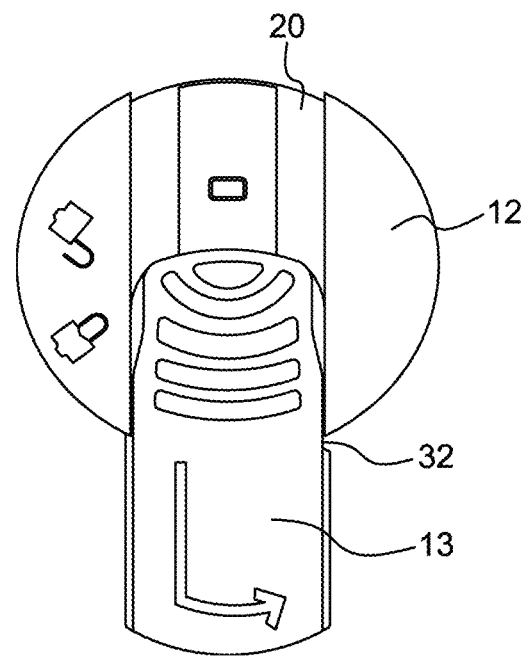

After the bump 31 on the slider 13 has passed over the bump 23a in the second groove 21, the ends of the parallel ridges 30a, 30b abut against the closed end 21a of the second groove 21 and the slider 13 cannot be slid any further across the cap 12. The ridges 30a, 30b and the ends 21a of the second groove 21 are positioned such that at this point, i.e.

when the parallel ridges 30*a*, 30*b* abut against the closed end 21*a* of the second groove 21, the curved groove 32 on the underside of the slider 13 extends around the outer circumference of the cap 12, as shown in FIGS. 12(*b*) and (*c*). The slider 13 should be slid into this position, i.e. where the ends of the parallel ridges 30*a*, 30*b* abut against the closed end 21*a* of the second groove 21 and the curved groove 32 on the underside of the slider 13 extends around the outer circumference of the cap 12 before the further steps of assembly of the lid 10 described below are performed.

Figure 13:
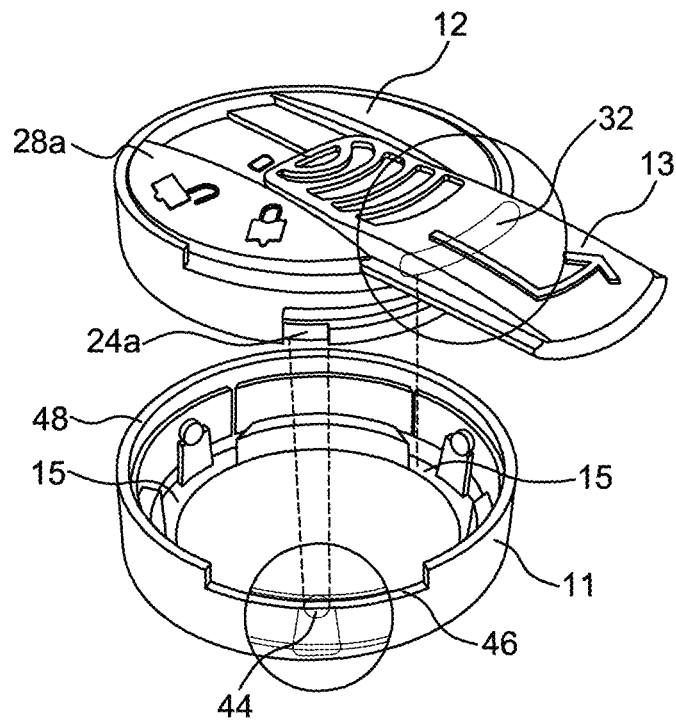
FIG. 13 shows how to insert the assembled cap of FIG. 12 into the assembled base of FIG. 10.

FIG. 13 shows how to insert the assembled cap 12 (i.e. with the slider 13 and sealing ring 14 inserted in it) into the assembled base 11 (i.e. with the pins 15 inserted in it).

The assembled cap 12 is positioned with its upper surface 28*a* facing upwards and the assembled base 11 is positioned, for example on a level surface, with its radially inwardly extending part 42 located at the bottom or facing downwards. The cap 12 is positioned such that the upwardly-extending parts 24*a* of the grooves 24 in the cap 12 are each located directly above a circular guide projection 44 in the base 11. The assembled cap 12 (with slider 13) is further positioned such that the slider 13 slightly overlaps the recess 46 in the side part 40 of the base 11.

The assembled cap 12 and the assembled base 11 are then pressed or snapped together, by pressing the cap 12 into the base 11, such that the circular guide projections 44 in the base 11 pass over the ridges 24*d* at the top end of each upwardly-extending part 24*a*, and into the circumferentially-extending parts 24*b*.

As the assembled cap 12 (i.e. including the slider 13) has been positioned such that the slider 13 slightly overlaps the recess 46 in the side part 40 of the base 11, part of the top edge 48 of the base 11 is fitted into the curved groove 32 on the underside of the slider 13.

Figure 14:
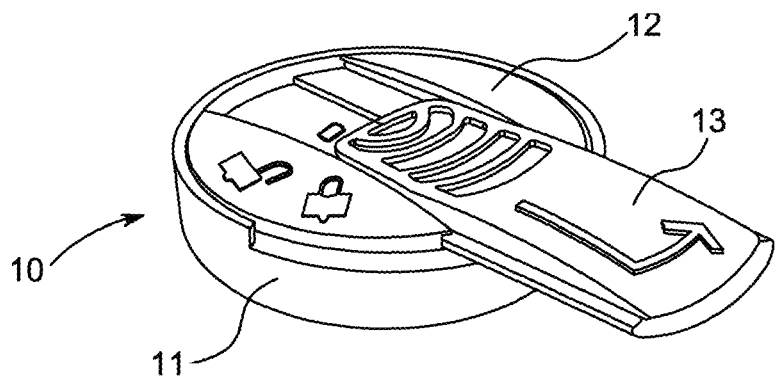
FIG. 14 shows a perspective view of a lid following the step of FIG. 13.

FIG. 14 shows a perspective view of a lid 10 comprising the base 11, cap 12 and slider 13 (as well as the pins 15 and sealing ring 14, which are not visible) following the steps associated with FIG. 13 described above.

Figure 15:
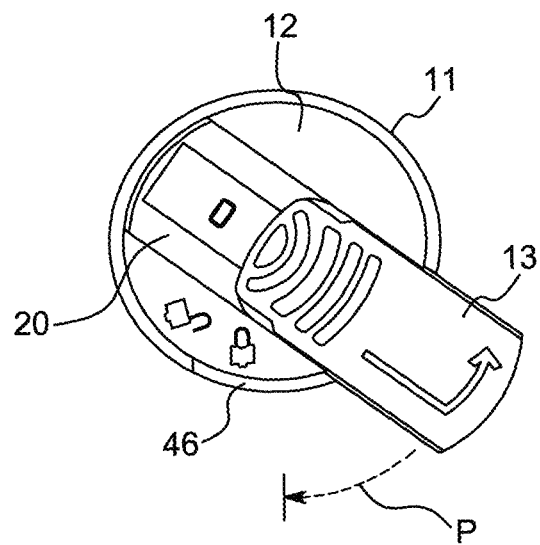
FIGS. 15(a)-(d) shows steps for finalising the assembly process of the lid following the step of FIG. 13.
Figure 15:
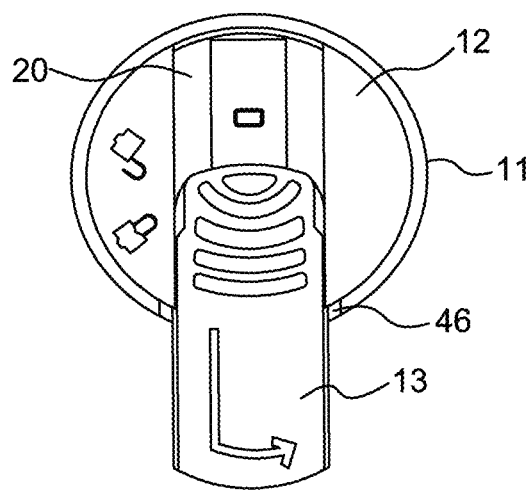
Figure 15:
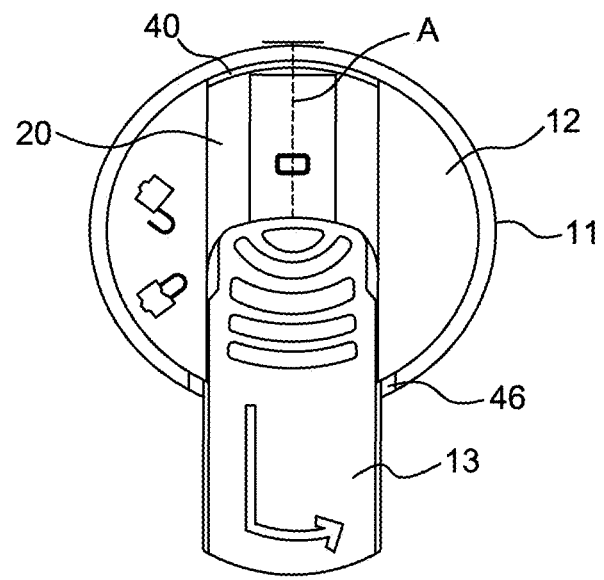
Figure 15:
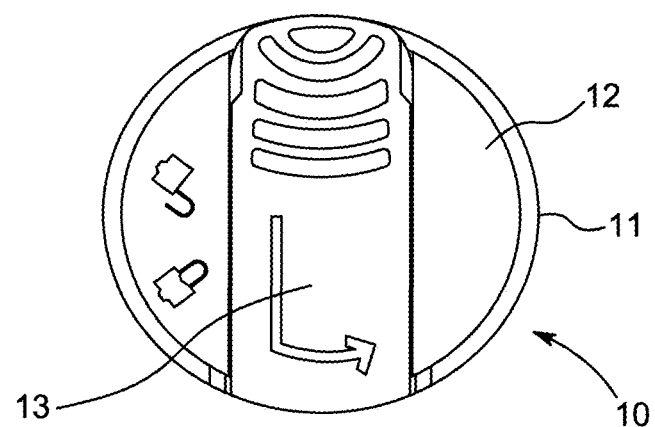

FIGS. 15(*a*)-(*d*) shows the steps for finalising the assembly process of the lid 10 following the steps of FIG. 13 described above.

First, the cap 12 and slider 13 are rotated clockwise with respect to the base 11, when viewed from above, by pushing the slider 13 along path P, as shown in FIG. 15(*a*). By pushing the slider 13, the cap 12 is rotated as far as it can be, i.e. until the circular guide projections 44 reach the upper ends of the circumferentially-extending parts 24*b* of the grooves 24 (opposite to the ends where the circumferentially-extending parts 24*b* meet the upwardly-extending parts 24*a*) and are thus prevented moving further.

As the cap 12 is rotated in this way, it is also drawn further down into the base 11 due to the slope of the circumferentially-extending parts 24*b* in the cap 12.

When the cap 12 has been rotated as far as it can be, i.e. when the circular guide projections 44 reach the upper ends the circumferentially-extending parts 24*b* of the grooves 24, the slider 13 is located inside the recess 46 of the base 11, as shown in FIG. 15(*b*).

Next, as shown in FIG. 15(*c*), the slider 13 is pushed inwards, along arrow A through the recess 46 and first groove 20, until it is prevented from moving further by abutting against the side part 40 of the base 11. At this point, the slider 13 is positioned across the entire diameter of the lid 10, within the first groove 20, as shown in FIG. 15(*d*). The longitudinal length of the slider 13 is equal to the outer diameter of the base 11 such that, at this point, the slider 13 does not project outwardly from base 11 at all.

Figure 16:
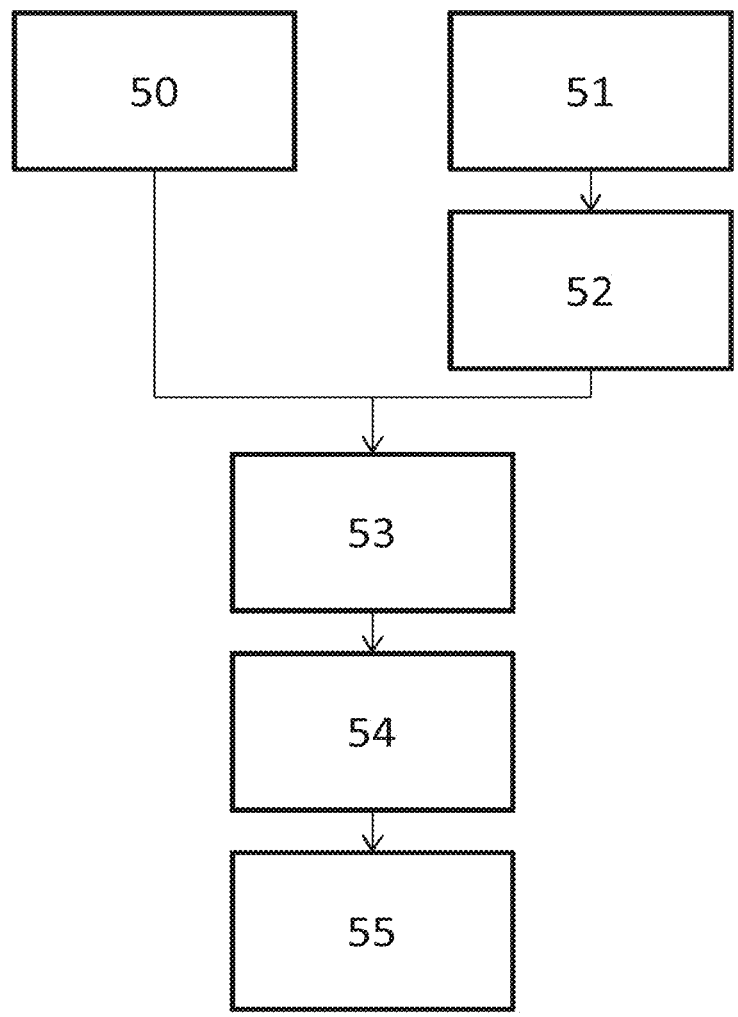
FIG. 16 is a flow diagram showing the steps for assembly of the lid.

FIG. 16 is a flow diagram showing the steps for assembly of the lid 10 from its component parts 11, 12, 13, 14, 15.

Figure 10:
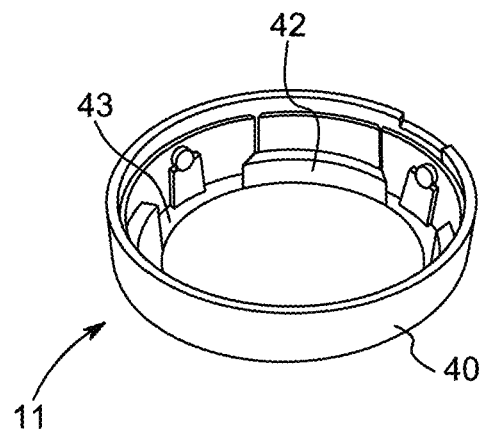
FIGS. 10(a)-(c) show steps for inserting the pins of FIG. 8 into the base of FIG. 7.
Figure 10:
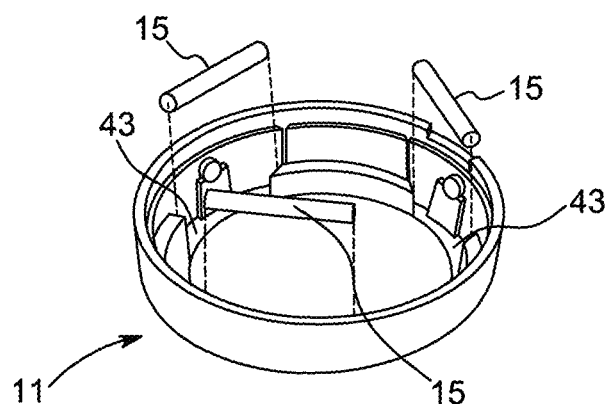
Figure 10:
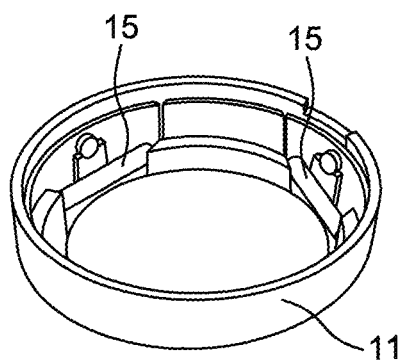

At step 50, the pins 15 are inserted into the base 11, as shown in FIGS. 10(*a*)-(*c*) and described above.

Figure 11:
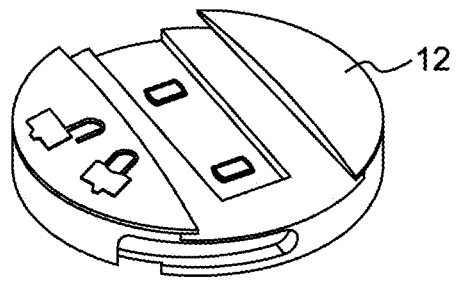
FIGS. 11(a)-(e) show steps for inserting the sealing ring of FIG. 9 into the cap of FIG. 5.
Figure 11:
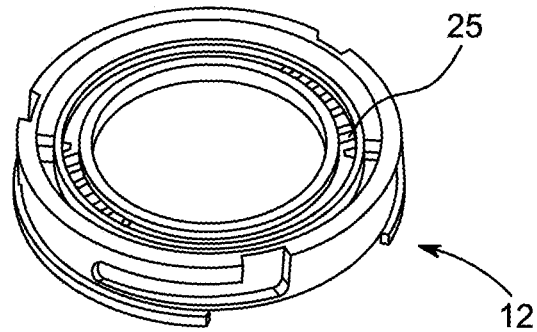
Figure 11:
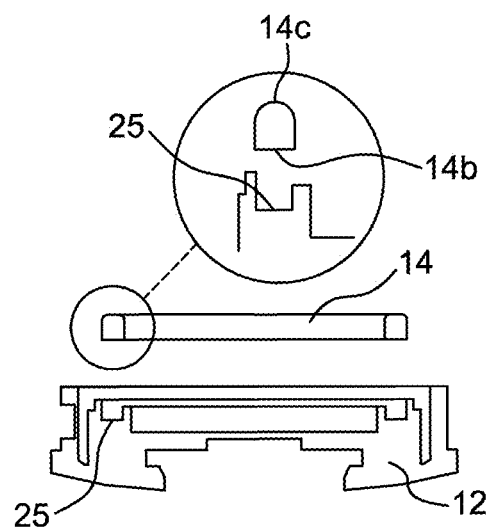
Figure 11:
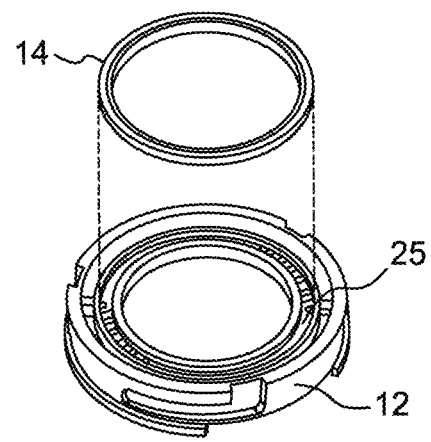
Figure 11:
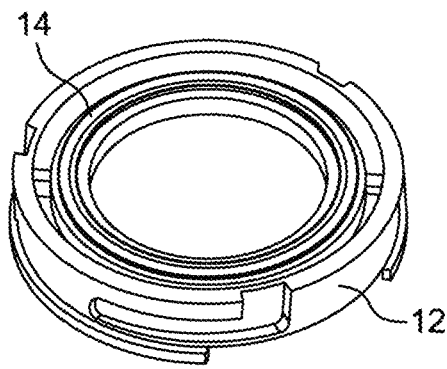

At step 51, the sealing ring 14 is inserted into the cap 12, as shown in FIGS. 11(*a*)-(*e*) and described above. In an alternative embodiment, in which the cap 12 and sealing ring 14 are/have been formed together (e.g. in a two-step injection moulding process, as described above), this step 51 is not needed.

At step 52, the slider 13 is inserted into the cap 12, as shown in FIGS. 12(*a*)-(*c*) and described above.

In FIG. 16, step 51 is performed before step 52 but in other embodiments step 52 is performed before step 51, and in yet other embodiments steps 51 and 52 are performed in parallel.

In FIG. 16, step 50 is performed in parallel with steps 51 and 52 but in other embodiments steps 50, 51 and 52 are performed in series in any order, e.g. 50 then 51 then 52; or 51 then 52 then 50. The other sequences of these steps would also be possible.

After steps 50-52 have been performed (in whichever order, and in series or in parallel), step 53 is performed in which the cap 12 (with the slider 13 and sealing ring 14) is inserted into the base 11 (with pins 15), as shown in FIGS. 13 and 14 and described above.

Next, at step 54, the cap 12 is rotated with respect to the base 11, as shown in FIGS. 15(*a*) and (*b*) and described above.

Finally, at step 55, the slider 13 is slide into the groove 20 in the cap 12, as shown in FIGS. 15(*c*) and (*d*) and described above, and is ready for packaging, use or storage.

Once the lid 10 has been assembled in this way, it can be provided to a patient for fitting onto an implant 1.

FIGS. 17(*a*)-(*d*) show steps for fitting the lid 10 onto an implant 1.

Starting from a lid 10 with the slider 13 slid in across the cap 12, before the lid 10 can be fitted on an implant 1, the slider 13 must be slid outwardly along the groove 30 in the cap 12. The cap 12 must then be rotated anti-clockwise with respect to the base 11 when viewed from above (or vice versa), such that the cap 12 rises up out of the base 11 slightly, and the slider 13 is only slightly overlapping the recess 46. The lid 10 is then ready to be fitted onto an implant 1.

As shown in FIG. 17(*a*) a user holds the projecting end of the slider 13 and places the lid 10 over the exterior section 4 of the implant 1.

The slider 13 is then used to hold the cap 12 stationary while the base 11 is rotated in an anti-clockwise direction with respect to the cap 12 when viewed from above, as shown by the arrow in FIG. 17(*b*) (alternatively, the slider 13 could be used to rotate the cap 12 in a clockwise direction with respect to the base 11 when view from above, while the base 11 is held stationary) until the slider 13 is positioned completely in the recess 46 of the base 11.

As the base 11 is rotated anti-clockwise with respect to the cap 12 (or vice versa), the cap 12 is drawn down into the base 11 by virtue of the circular guide projections 44 being made to slide along upwardly sloping circumferentially-extending parts 24*b* of the grooves 24 around the cap 12.

As the cap 12 is drawn down into the base 11 in this way, the side part 29 of the cap 12 moves down into the circumferential groove 45 inside the base 11, thereby forcing the three pins 15 located in the three straight grooves 43 around the circumferential groove 45 radially inwardly, against the resilient tongues 49 and slightly upwardly into the groove 6 around the exterior circumference of the exterior section 4 of the implant 1. This engaging of the pins 15 against the inner upper surface of the groove 6 of the implant 1 secures and holds the lid 10 onto the implant 1 and prevents users from being able to simply move or pull the lid 10 straight off of the implant 1, intentionally or unintentionally.

In addition, as the cap 12 is drawn down into the base 11, the sealing ring 14 on the underside of the cap 12 is compressed against the upper surface of the exterior section 4 of the implant 1 thereby forming a leak-proof seal between the implant 1 and the lid 10.

Once the lid 10 has been secured and sealed in this way, the slider 13 is slid back across the rest of the lid 10, through groove 20, as shown in FIG. 17(c), so that it is no longer protruding radially outwardly from the rest of the lid 10, as shown in FIG. 17(d).

In order to remove a lid 10 from an implant 1, the reverse procedure is performed, as shown in FIGS. 18(a)-(d).

The lid 10 starts with the slider 13 in a "slid in" position with respect to the rest of the lid 10, as shown in FIG. 18(a). The slider 13 is then pulled outwards through the groove 20 in the cap 12, as shown in FIG. 18(b). When fully drawn out, the slider 13 is then used to hold the cap 12 stationary while the base 11 is rotated in a clockwise direction with respect to the cap 12 (or, alternatively, the base 11 is held stationary and the slide 11 is used to rotate the cap 12 in an anti-clockwise direction with respect to the base 11). This rotation causes the cap 12 to move upwards and slightly out of the base 11 such that the side part 29 no longer forces or holds the pins 15 in the groove 6 around the implant 1 and the resilient tongues 49 cause the pins 15 to be retracted from the groove 6. In addition, the sealing ring 14 is no longer compressed down against the upper surface of the exterior section 4 of the implant 1.

The user can then lift the lid 10 off of the implant 1 with little or no resistance.

After removal of the lid 10 in this way from an implant 1, it should be washed, as shown in FIG. 18(e).

Figure 19:
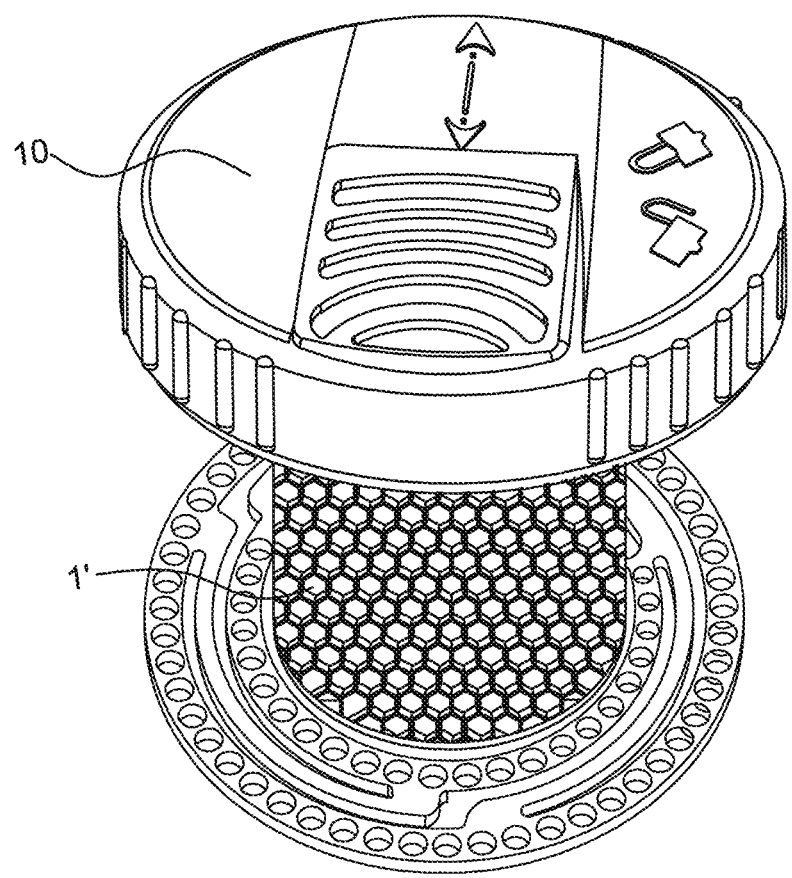
FIG. 19 shows a perspective view of an implant fitted with a lid of FIG. 3.

FIG. 19 shows a perspective view of an implant 1' (not implanted in a patient) fitted with a lid 10.

The lid 10 is reusable but with a limited life. It can be used by a patient for up to two weeks before a new lid 10 must be used.

The lid 10 is dimensioned to fit an implant with an outer diameter corresponding to an inner diameter of the lid 10. However, the lid 10 can be fitted onto implants 1, 1' with differing axial lengths and/or different internal structures.

The slider 13, the cap 12 and the base 11 are all made of plastic by injection moulding.

The pins 15 are made of stainless steel.

In an alternative embodiment, the pins 15 are made of plastic. This can ensure that the pins 15 wear out long before the edge of the groove 6 in the implant 1, 1' over which the pins 15 move.

The sealing ring 14 is made of a medical grade soft polymer.

Each lid 10 is provided to a user in a disinfected state in a semi-sealed individual bag (i.e. the bags are perforated along one side to be easy to tear open. However, the lid 10 does not need to be sterile.

The lid 10 (except the pins 15 and sealing ring 14) is skin-coloured and is intended to be inconspicuous.

The lid 10 is designed such that one lid size can fit different implant sizes. For example, implants can be provided with different inner diameters (i.e. the diameter of the opening through the implant), e.g. optimised for different sizes (thicknesses/diameters) of ileum. However, as the implants (particularly their exterior sections) have the same outer diameter, the same lid 10 may fit implants with different inner diameters.

The sealing ring 14 is located sufficiently close to the outer diameter of the lid 10 such that the lid 10 may fit implants even with a relatively large inner diameter (and, consequently, a relatively thin exterior section top surface against which the sealing ring 14 can be compressed).

The lid 10 can also fit implants with different axial lengths, providing that the outer diameter of the exterior section of the implant is the same.

The fact that the same lid 10 may fit implants of different sizes is advantageous because there is no need to make different sized lids for implants with different inner diameters and/or axial lengths. This makes manufacturing simpler, saves time and costs, and is safer (there is no chance of putting a wrong sized lid 10 on an implant).

What is claimed:

1. A lid for a medical implant, the lid comprising:
    a first part;
    a second part; and
    a seal;
    wherein;
        the seal is provided in, or as a part of, the first part;
        the first part is configured to be assembled with the second part to form an assembled lid prior to the assembled lid being placed over the implant; and
        when the assembled lid is placed over the implant, rotation of the first part relative to the second part causes the first part to be drawn towards, into, onto, further into, or further onto the second part, thereby attaching the assembled lid to the implant and compressing the seal against the implant, so as to seal the implant.

2. The lid according to claim 1, wherein the seal is provided on a side of the lid that is configured to face the implant, when the lid is attached to the implant.

3. The lid according to claim 1, comprising an engaging unit for engaging the lid with the implant.

4. The lid according to claim 3, wherein the lid is arranged such that, when the first part is assembled with the second part and the lid is placed over the implant, rotation of the first part relative to the second part causes the first part to engage the engaging unit which thereby engages the implant, thereby attaching the lid to the implant.

5. The lid according to claim 4, wherein the engaging unit is configured to engage with the implant by being, at least partly, displaced radially inwards.

6. The lid according to claim 3, wherein the engaging unit comprises one fixed part and one movable part.

7. The lid according to claim 6, wherein the fixed part comprises a fixed edge, ridge or other protrusion provided on the lid for engaging with a corresponding groove or indentation on the implant or vice versa.

8. The lid according to claim 7, wherein the edge, ridge or other protrusion is provided on or around a lower inner rim of the lid.

9. The lid according to claim 7, wherein the edge, ridge or other protrusion covers half or less than half of an inner circumference of the lid.

10. The lid according to claim 6, wherein the movable part comprises a lever, pin, hook or other movable engaging unit.

11. The lid according to claim 3, wherein the engaging unit is located in the second part or wherein the engaging unit is integrally formed with the second part, and wherein the engaging unit is movable, at least to some extent, with respect to a side of the second part.

12. The lid according to claim 1, wherein the first part comprises a rotation unit for facilitating rotation of the first part relative to the second part.

13. The lid according to claim 12, wherein the rotation unit is a slider arranged to slide radially in a groove.

14. The lid according to claim 12, wherein the rotation unit is movable between a first position in which the second part may be rotated relative to the first part, and a second position in which the second part may not be rotated relative to the first part.

15. The lid according to claim 1, wherein the lid comprises a locking unit, for locking/unlocking the lid.

16. The lid according to claim 15, wherein the locking unit is a rotation unit for facilitating rotation of the first part relative to the second part.

17. The lid according to claim 15, wherein the lid comprises a feedback unit for providing tactile and/or audible feedback to a user for indicating when the lid is in locked/unlocked states/positions.

18. The lid according to claim 17, wherein the feedback unit comprises at least one bump, ridge or groove provided under the locking unit.

* * * * *